(12) United States Patent
del Nido et al.

(10) Patent No.: US 8,491,631 B2
(45) Date of Patent: Jul. 23, 2013

(54) TISSUE TACK

(75) Inventors: Pedro J. del Nido, Lexington, MA (US);
Nikolav V. Vasilyev, Belmont, MA (US);
Franz Freudenthal, La Paz (BO);
Pierre Dupont, Wellesley, MA (US);
Jinlan Huang, Wayland, MA (US)

(73) Assignees: Children's Medical Center Corporation, Boston, MA (US); Trustees of Boston University, Boston, MA (US); National Institutes of Health (NIH), U.S. Dept. Of Health And Human Sevices (DDHHS), The United States of America, Washington, DC (US)

( * ) Notice: Subject to any disclaimer, the term of this patent is extended or adjusted under 35 U.S.C. 154(b) by 452 days.

(21) Appl. No.: 12/162,633

(22) PCT Filed: Jan. 3, 2007

(86) PCT No.: PCT/US2007/002644
§ 371 (c)(1),
(2), (4) Date: Dec. 16, 2008

(87) PCT Pub. No.: WO2007/089843
PCT Pub. Date: Aug. 9, 2007

(65) Prior Publication Data
US 2009/0306681 A1 Dec. 10, 2009

Related U.S. Application Data

(60) Provisional application No. 60/763,260, filed on Jan. 30, 2006, provisional application No. 60/781,034, filed on Mar. 10, 2006, provisional application No. 60/746,188, filed on May 2, 2006.

(51) Int. Cl.
*A61B 17/08* (2006.01)
*A61B 17/10* (2006.01)
*A61B 17/56* (2006.01)
*F16B 15/00* (2006.01)

(52) U.S. Cl.
USPC .............. 606/219; 606/75; 606/142; 411/358

(58) Field of Classification Search
USPC ................... 606/75, 142, 219, 104, 151, 153, 606/232; 227/175.1; 411/439, 456, 451.2, 411/457–459, 473, 358, 359; 600/104
See application file for complete search history.

(56) References Cited

U.S. PATENT DOCUMENTS 1,241,054 A * 9/1917 Tervo ............................. 411/473
4,887,601 A * 12/1989 Richards ....................... 606/219
(Continued)

FOREIGN PATENT DOCUMENTS
WO WO2004/112652 12/2004

OTHER PUBLICATIONS

Extended European Search Report, EP 07762739.6, mailed Dec. 2, 2011, 6 pages.

(Continued)

*Primary Examiner* — Julian Woo
(74) *Attorney, Agent, or Firm* — Fish & Richardson P.C.

(57) ABSTRACT

A tissue fixation device includes a tack having at least two flexible arms on a first end of said anchor. A deployment device for deploying a tissue fixation device, wherein the deployment device is a deployment gun.

6 Claims, 31 Drawing Sheets

U.S. PATENT DOCUMENTS

| | | | |
|---|---|---|---|
| 5,242,457 A * | 9/1993 | Akopov et al. | 227/175.1 |
| 5,263,973 A | 11/1993 | Cook | |
| 5,289,963 A * | 3/1994 | McGarry et al. | 227/175.1 |
| 5,632,717 A * | 5/1997 | Yoon | 600/104 |
| 6,200,330 B1 * | 3/2001 | Benderev et al. | 606/232 |
| 6,530,933 B1 | 3/2003 | Yeung et al. | |
| 6,776,784 B2 * | 8/2004 | Ginn | 606/151 |
| 7,326,231 B2 * | 2/2008 | Phillips et al. | 606/153 |
| 7,556,647 B2 * | 7/2009 | Drews et al. | 606/142 |
| 2001/0039435 A1 | 11/2001 | Roue et al. | |
| 2003/0065346 A1 | 4/2003 | Evens et al. | |
| 2003/0130669 A1 | 7/2003 | Damarati | |
| 2004/0193191 A1 | 9/2004 | Starksen et al. | |
| 2004/0236419 A1 | 11/2004 | Milo | |
| 2005/0004576 A1 | 1/2005 | Benderev | |
| 2005/0055027 A1 | 3/2005 | Yeung et al. | |
| 2005/0080454 A1 | 4/2005 | Drews et al. | |

OTHER PUBLICATIONS

International Search Report & Written Opinion, PCT/US07/02644, mailed Oct. 19, 2007, 8 pages.

* cited by examiner

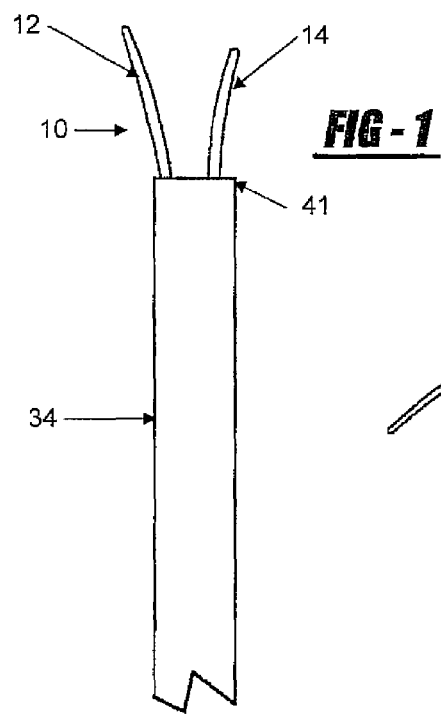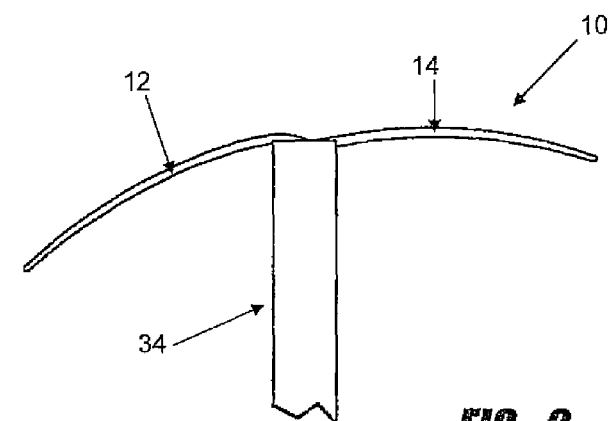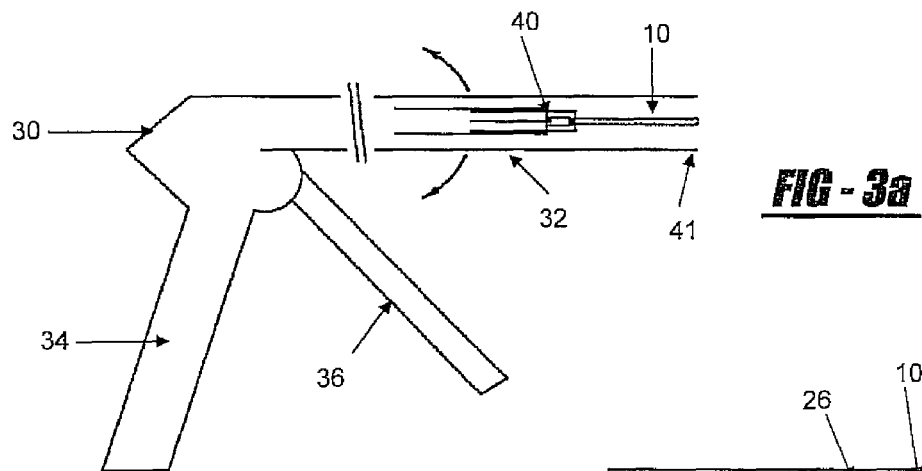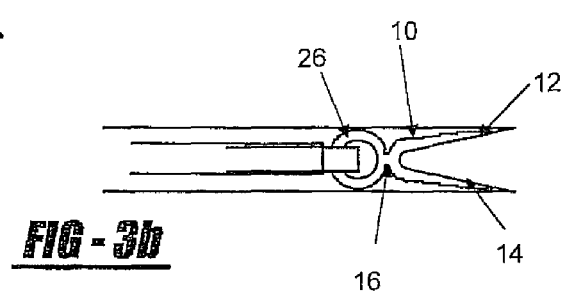

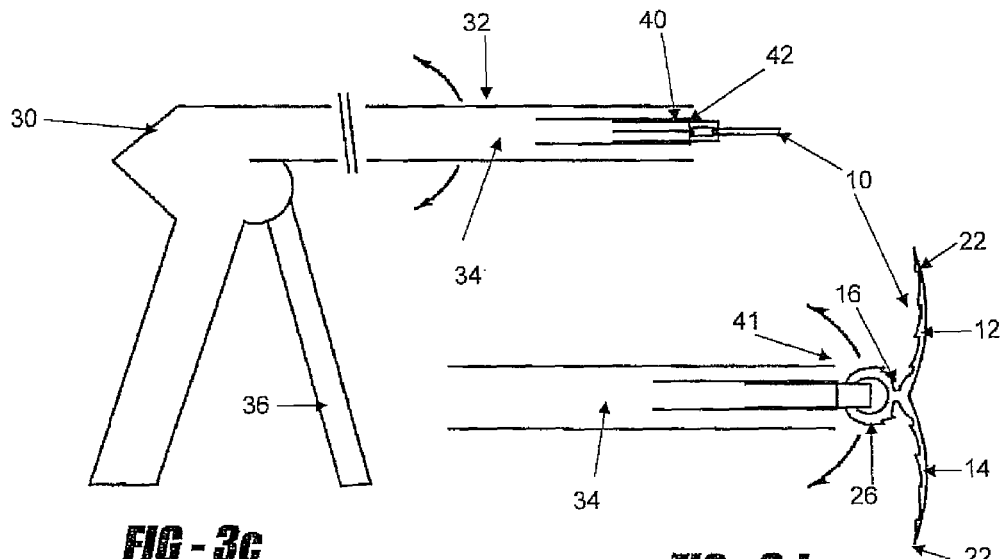
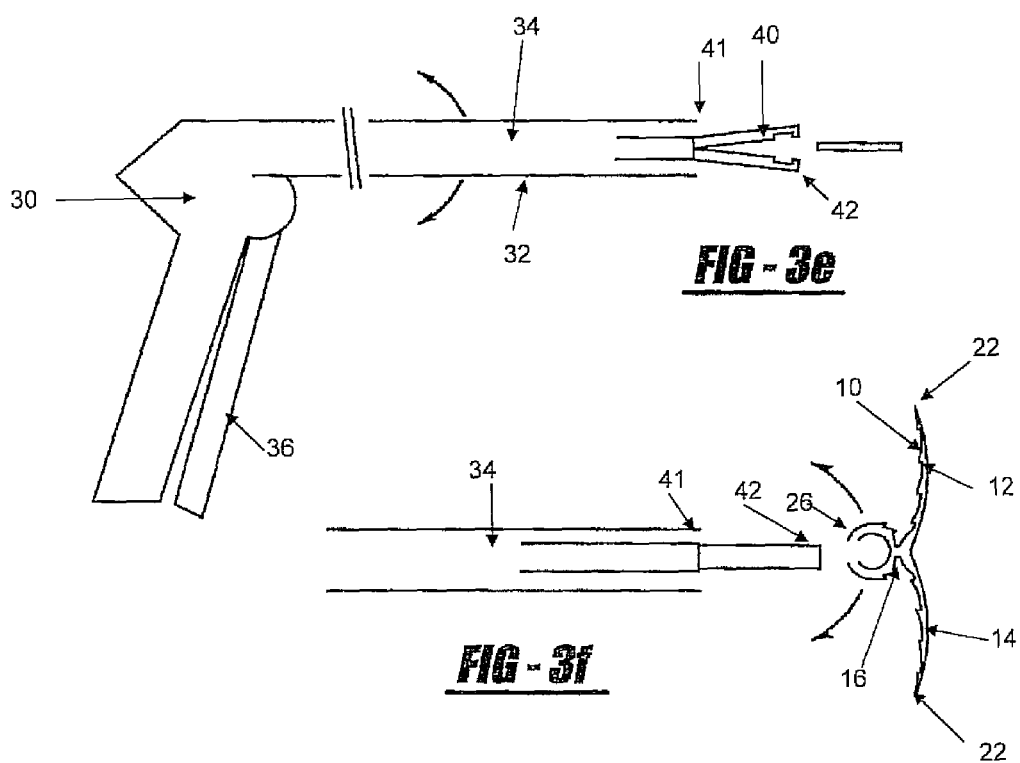

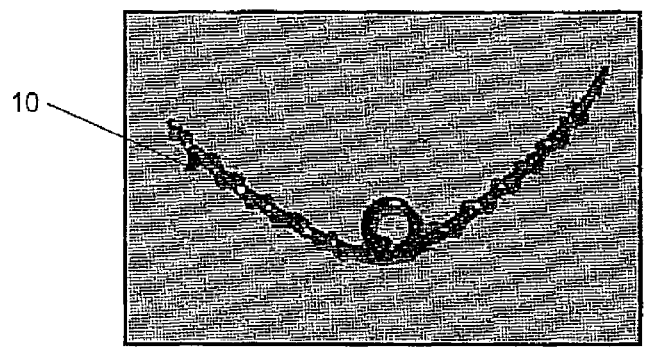
*FIG-5*
*FIG-6*
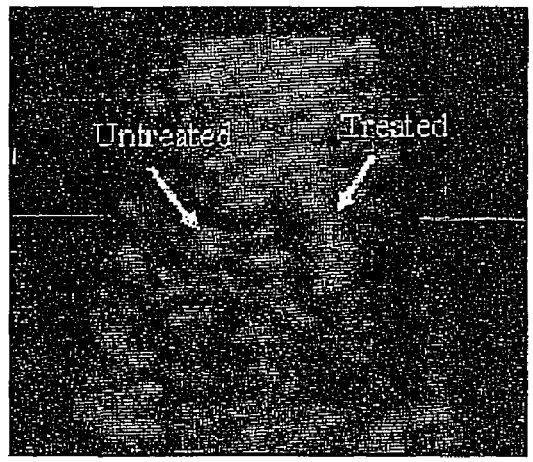
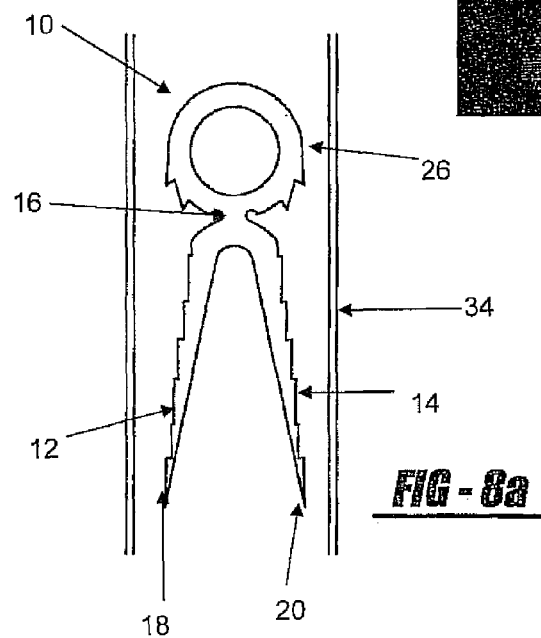
*FIG-8a*

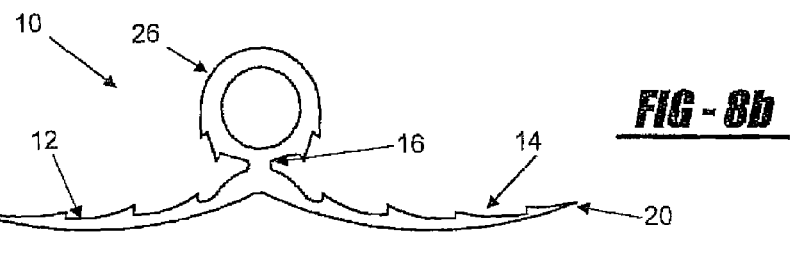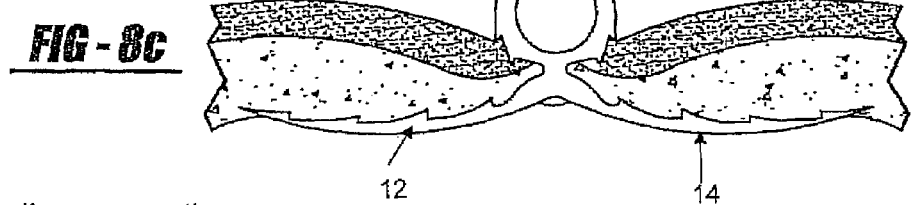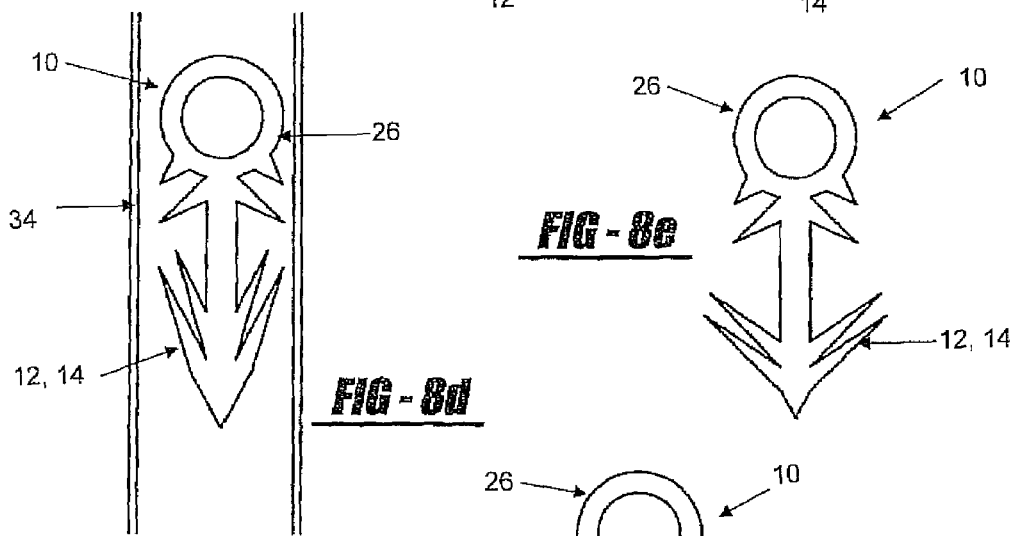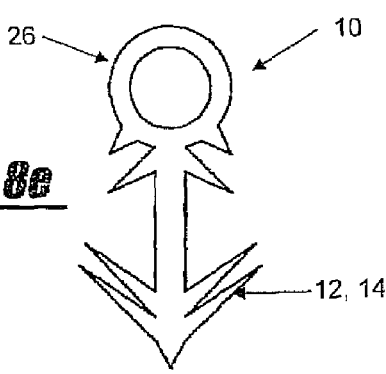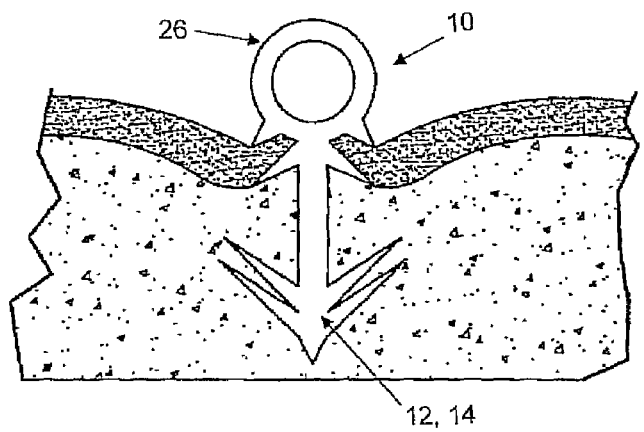

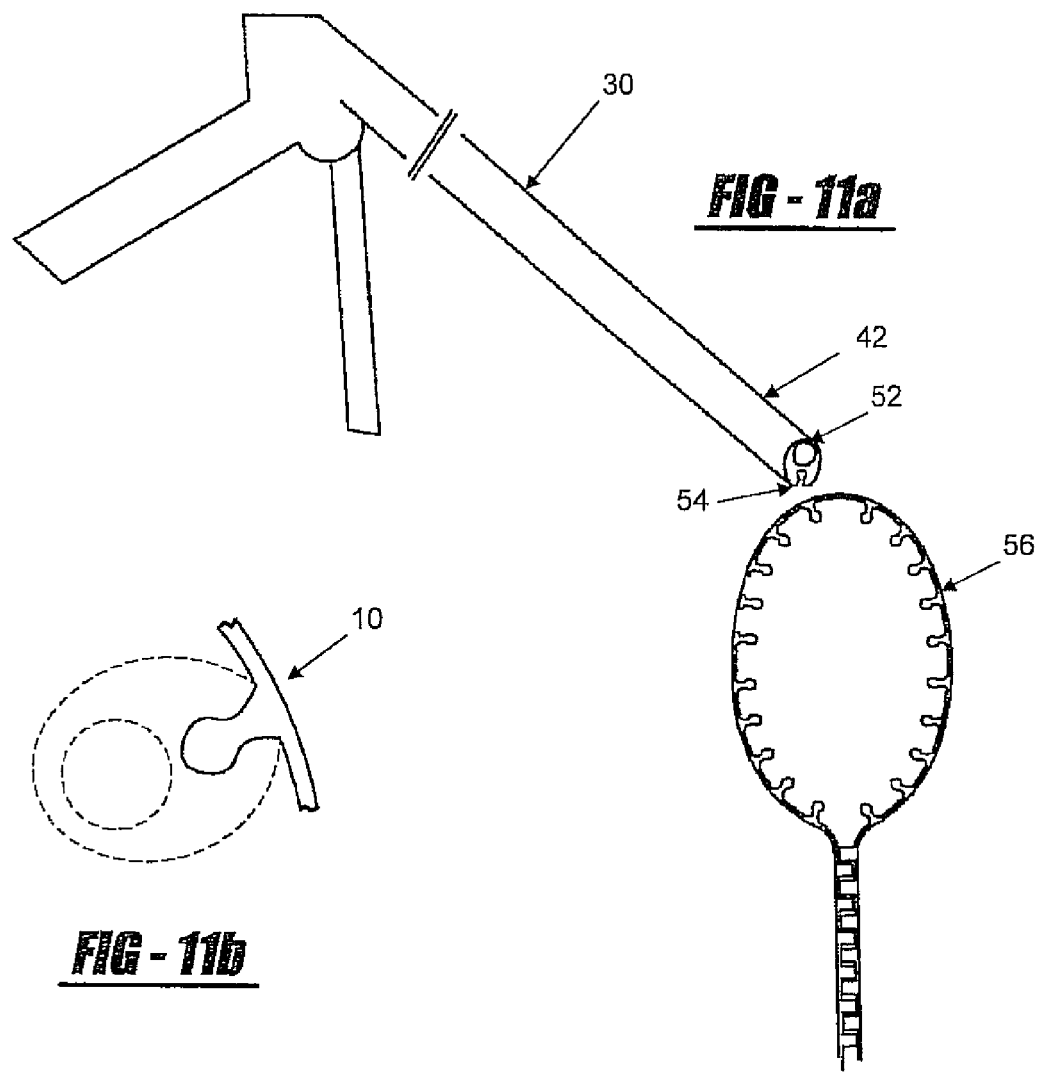
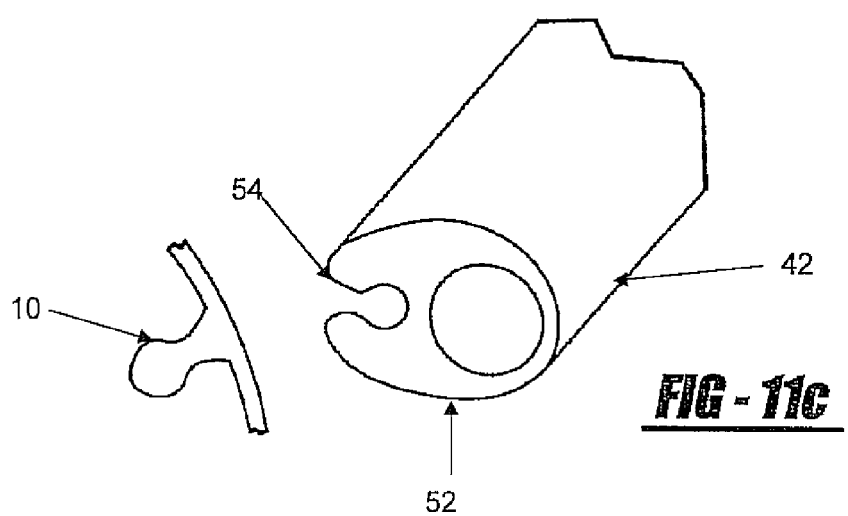

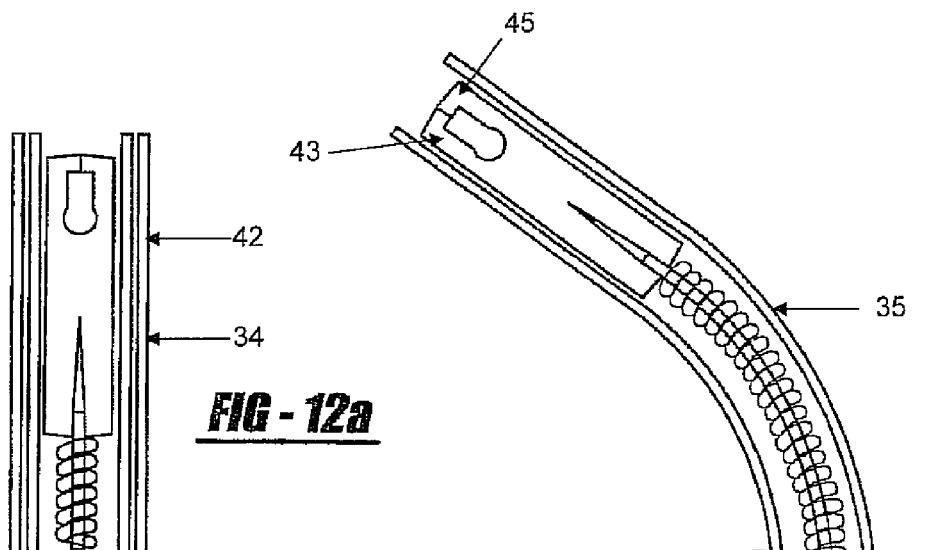
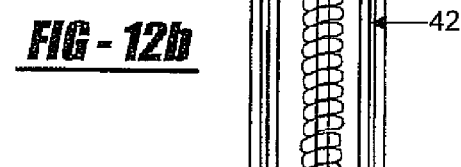
*FIG - 12a*
*FIG - 12b*
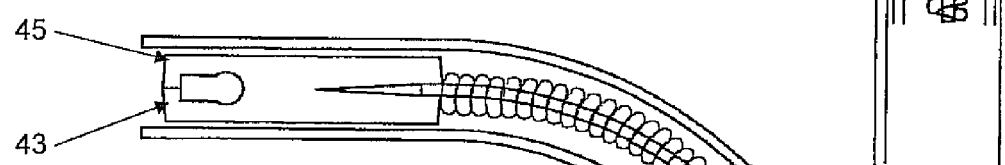
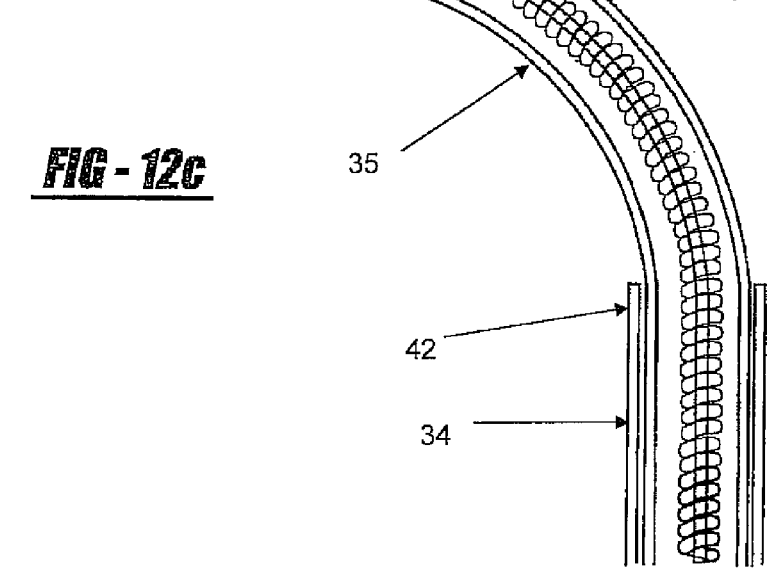
*FIG - 12c*

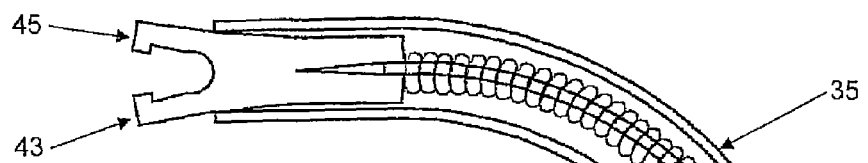
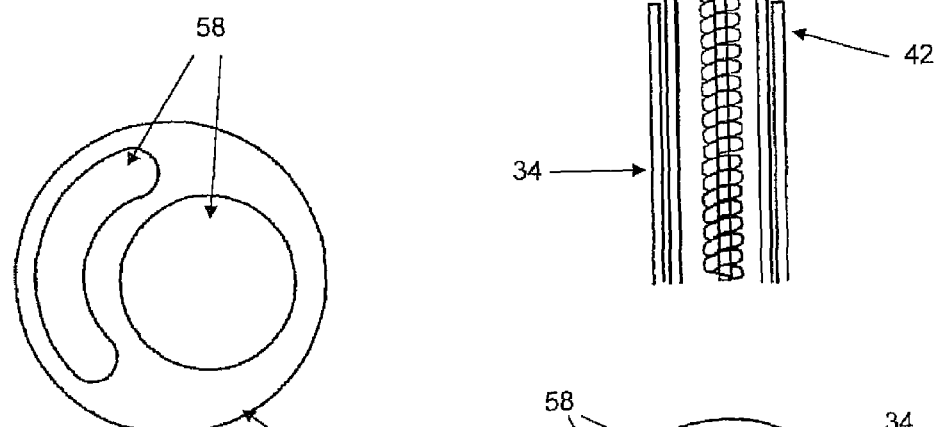
FIG - 12d
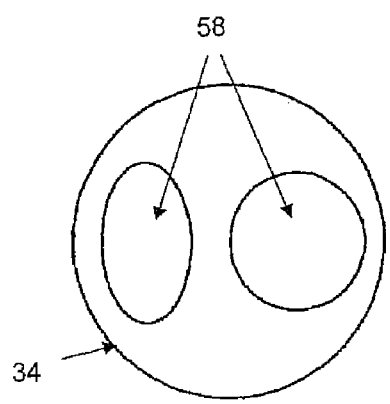
FIG - 13a
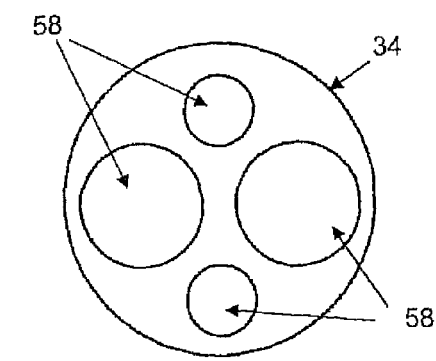
FIG - 13b
FIG - 13c

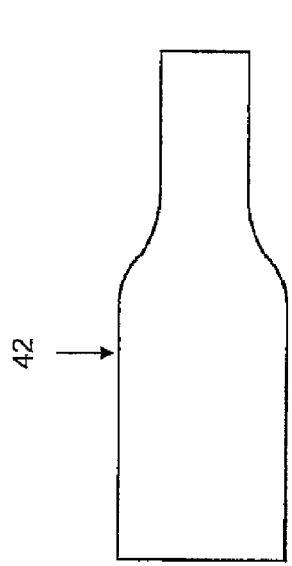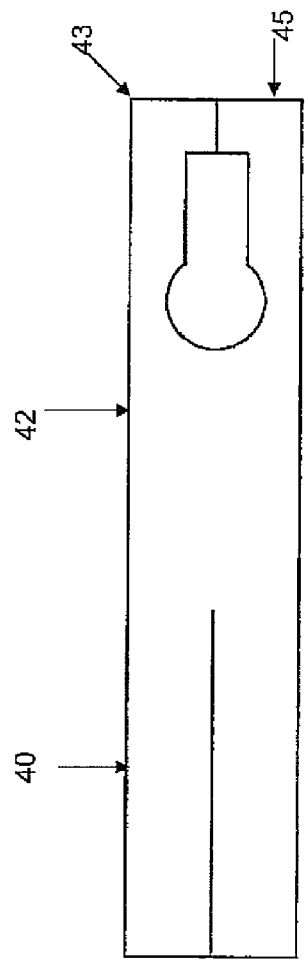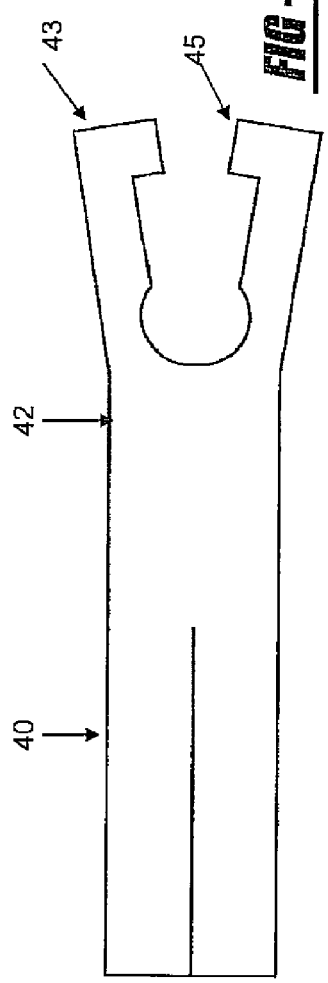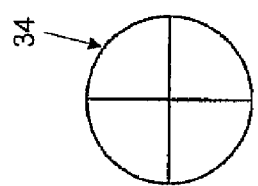

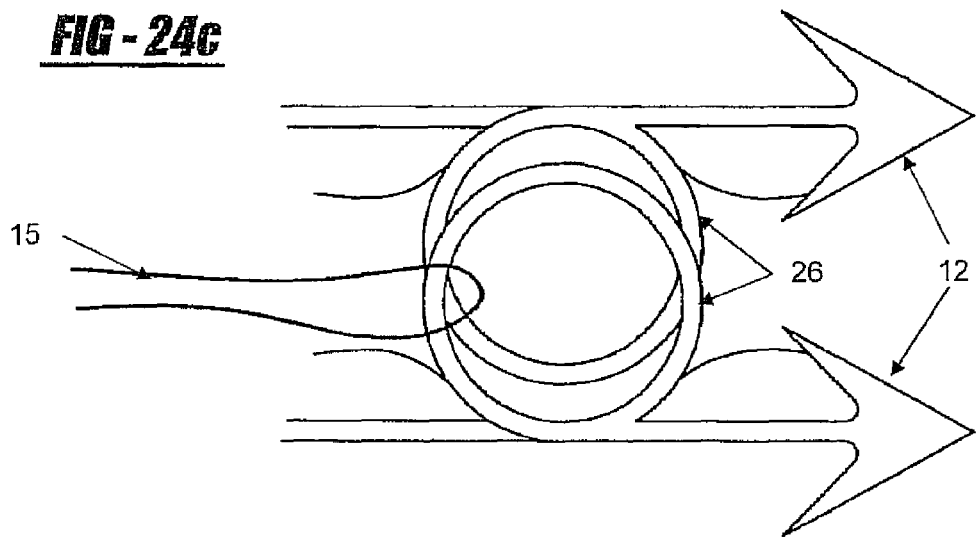
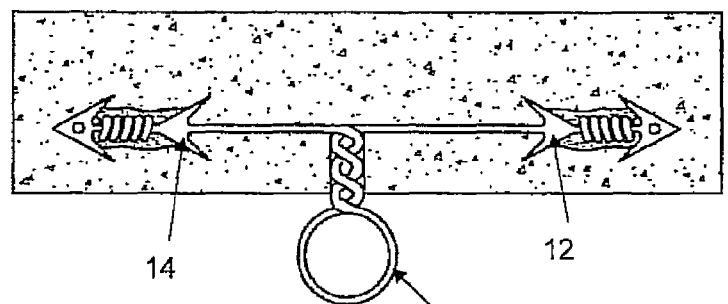
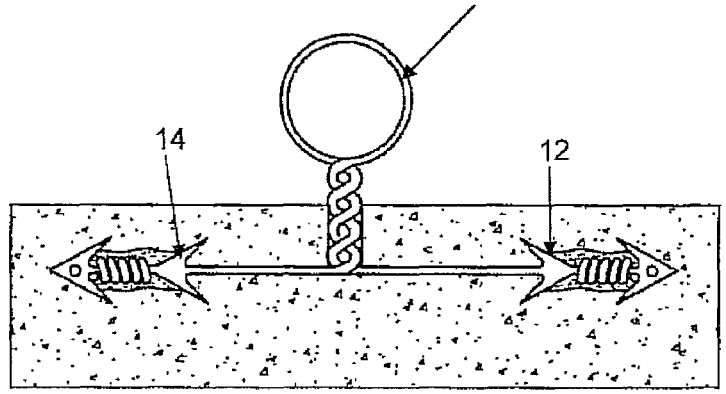

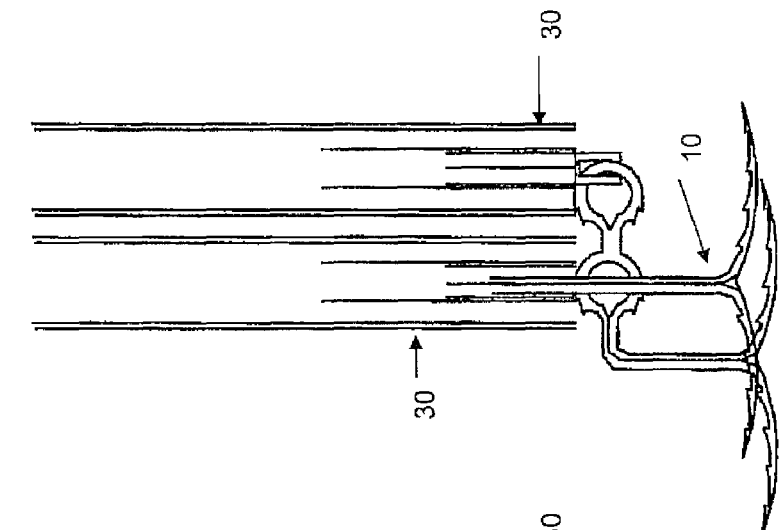
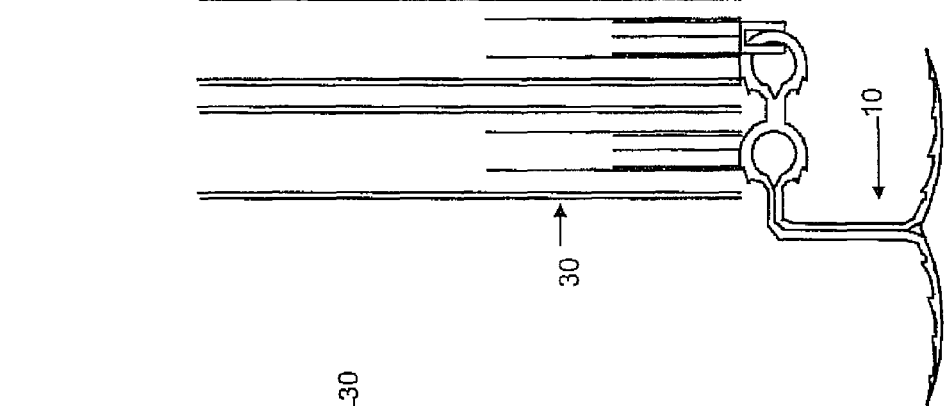
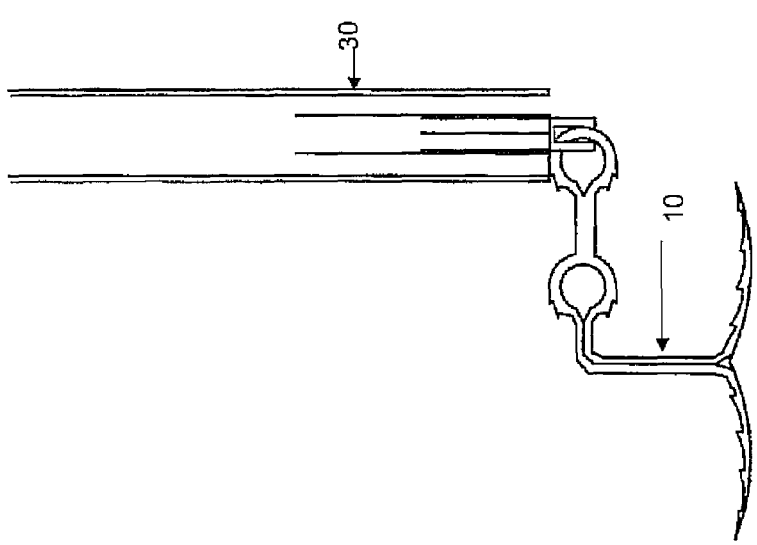

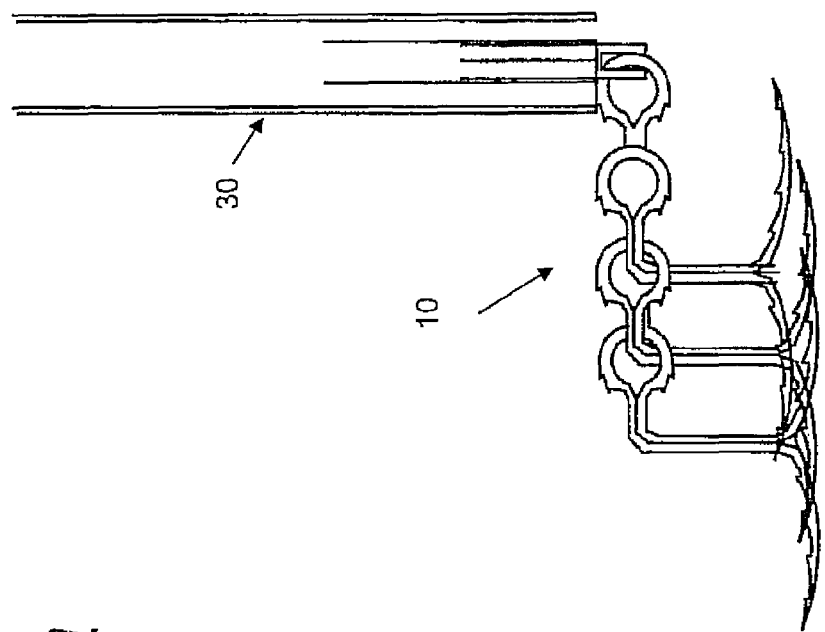
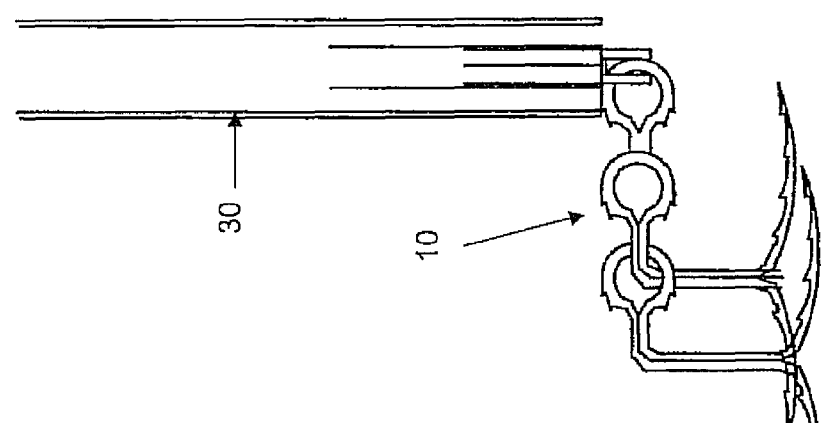
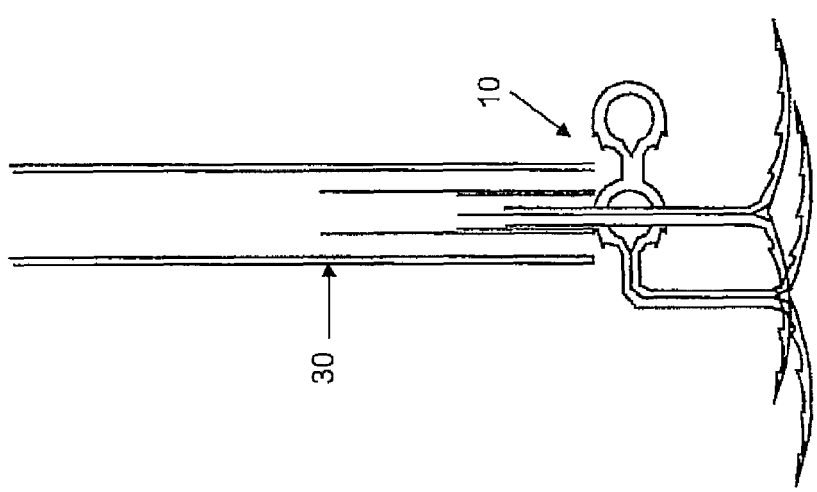

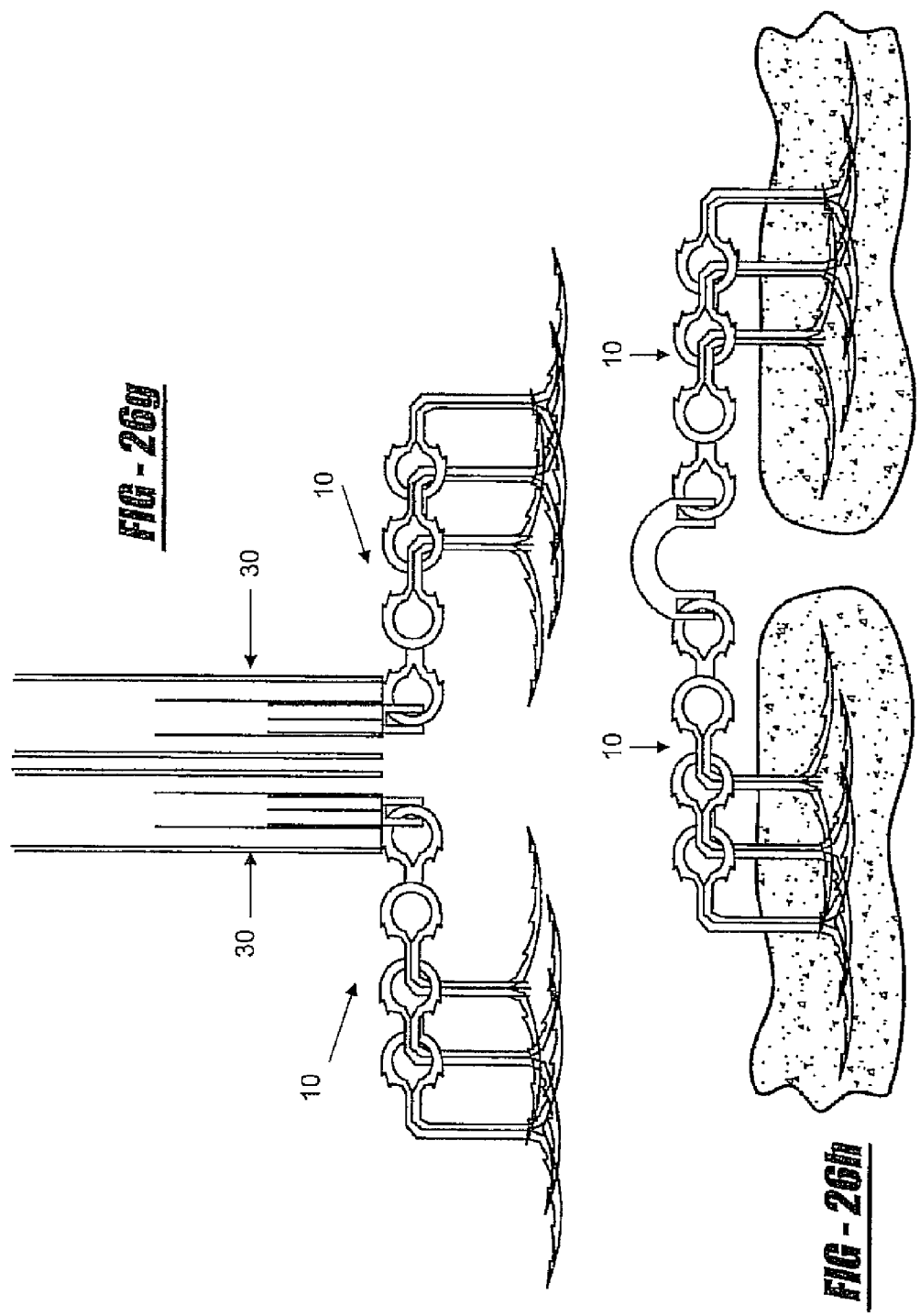

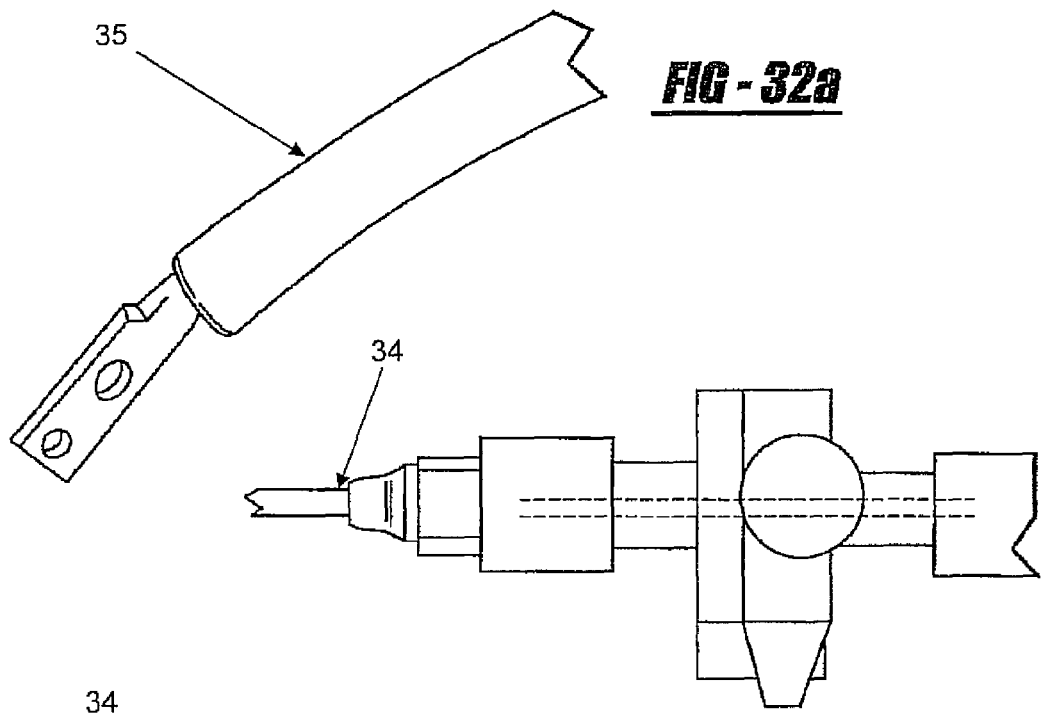
FIG-32a
FIG-32b
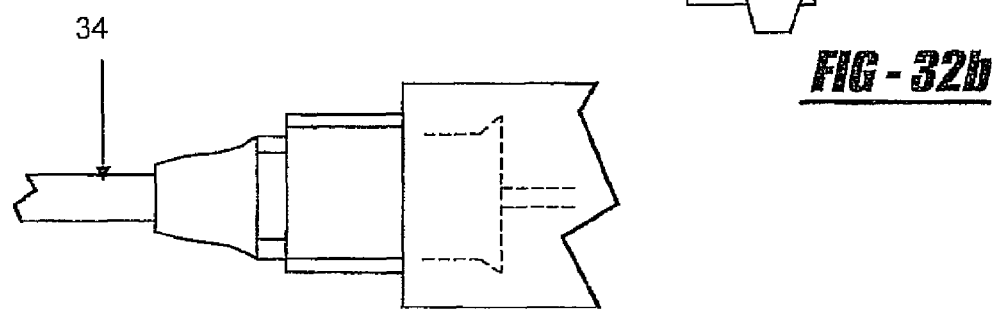
FIG-32c
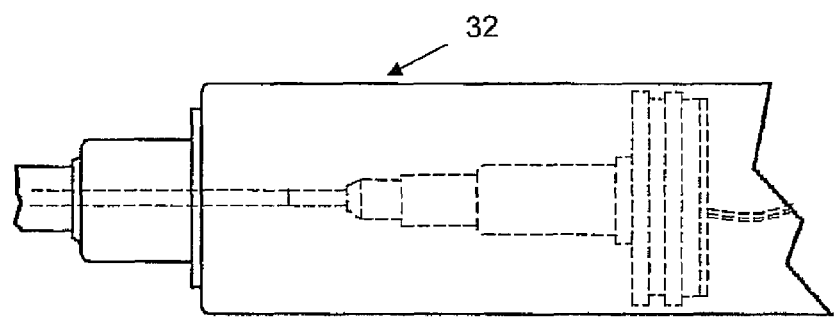
FIG-32d

TISSUE TACK

CROSS-REFERENCE TO RELATED APPLICATIONS

This is a National Phase Filing Under 35 U.S.C. 371, of International Application No. PCT/US07/02644, filed Jan. 30, 2007, which claims the benefit of priority of U.S. Provisional Patent Application Ser. No. 60/746,188, filed 1 May 2, 2006, which claims the benefit of priority of U.S. Provisional Patent Application Ser. No. 60/763,260, filed Jan. 30, 2006, which claims the benefit of priority of U.S. Provisional Patent Application Ser. No. 60/781,034, filed Mar. 10, 2006 all of which are incorporated herein by reference.

BACKGROUND OF THE INVENTION

1. Field of the Invention

Generally, the present invention relates to surgical devices. More specifically, the present invention relates to surgical devices for closing incisions, and fastening tissues and prostheses.

2. Description of Related Art

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, generally 3-10 millimeters. A number of such cannulas are inserted for any given operation.

A viewing instrument, typically including a miniaturized video camera, is inserted through one of these cannulas and a variety of surgical instruments and retractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from Dacron or Teflon) or are prepared as autografts (from the patient's own tissues) or heterografts (from the tissues of animals). A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Minimally invasive surgery is of interest in cardiovascular surgery because of the nature of the tissue of the heart. Cells known as myocytes beat together in unison in a healthy heart when ion channels open and close in an organized manner. Ions pass in and out of the channels, and the change in concentration of ions from within a cell to outside of a cell results in an electrical potential, causing the cell itself to depolarize and repolarize. The depolarization of one cell triggers the cell next to it to depolarize, and thus a cascade effect of depolarization of all the myocytes is triggered and the heart beats. Making several incisions can interrupt this cascade during surgery and change the beating of the heart. Keeping incisions to a minimum with minimally invasive techniques will allow beating heart surgery to be successful while maintaining the electrical integrity of the heart.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. In some minimally invasive procedures, such as those in the abdominal cavity, the retroperitoneal space, or chest, the space in which the operation is performed is more limited. The exposure to the involved organs is also more restricted than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

Recent advances in medical imagining technology coupled with advances in computer-based image processing and modeling capabilities have given physicians an unprecedented ability to visualize anatomical structures in live patients, and to use this information in diagnosis and treatment planning. The precision of image-based pre-surgical planning often greatly exceeds the precision of actual surgical execution. Precise surgical execution has been limited to procedures, such as brain biopsies, in which a suitable sterotactic frame is available. The inconvenience and restricted applicability of such a frame or device has led many researchers to explore the use of robotic devices to augment a surgeon's ability to perform geometrically precise tasks planned from computed tomography (CT) or other image data. The ultimate goal of this research is partnership between a man (the surgeon) and machines (computers and robots), that seeks to exploit the capabilities of both, to do a task better than either can do alone. Machines are very precise and untiring and can be equipped with any number of sensory feedback devices. Numerically controlled robots can move a surgical instrument through an exactly defined trajectory with precisely controlled forces. On the other hand, surgeons are very dexterous. They are also quite strong, fast, and are highly trained to exploit a variety of tactile, visual, and other cues. "Judgmentally" controlled, a surgeon understands what is going on in the surgery and uses dexterity, senses, and experience to execute the procedure. However, the surgeon usually wants to be in control of everything that goes on. If the surgeons desire to increase precision within acceptable limits of time or with sufficient speed, they must be willing to rely on machines to provide the precision.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by an applying instrument about the tissues in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be grasped and properly positioned with respect to each other, for example by skewering the tissues with a needle as in common suturing techniques and/or with forceps to bring the tissues together. As discussed, it is extremely difficult to perform such positioning techniques in minimally invasive procedures. Coalescent Surgical, Inc. also produces the U-CLIP Anastomotic Device based on self-closing clip technology of nitinol, which eliminates knot tying. The disadvantage of this system is that the surgeon needs to guide the needle from the graft through the native tissue before the U-CLIP can be deployed to suture the tissue. Therefore, there is a need for a system that does not require the surgeon to add an additional step of actively piercing the tissue before applying a suture in anastomosis. There is also a need for a system that has an automatic knot to keep the suture from migrating in the tissue, so that one would not need to be tied by hand by the surgeon. Other sutures have pointed ends that stick out and are not well suited for microsurgery within a tissue or hollow tissue. This can be uncomfortable for the patient, so a suture that has a low profile end sticking out of the tissue is needed. It is also of interest to develop a suture that can be used in beating heart surgery in order to affix a periocardial patch in the heart.

Besides the minimal invasive surgery, a new stage of treatment has been performed with interventional cardiology that is based in the use of balloons, stents, and other devices. The balloons occlude the vessels such that the therapies must be very short. Also, it is not simple to find the exact site of injury. The devices commonly used are occluders systems, coils, or umbrellas. Although these devices are able to fix a defect, the effectiveness of the device depends on the expertise of the surgeon to find the ideal device for the defect. This is important because after the implantation, the defect adapts itself to the device, specifically the umbrellas.

The occluder devices like the umbrellas type have numerous disadvantages, including, but not limited to, a negative effect in the heart compliance and a negative effect in the dynamic heart development. Negative effects in the cardiac conduction system, in conjunction with blockades, can lead a patient to a sudden death. There is a source of thrombotic formation in the left side that can cause serious neurological complications and can also produce perforations of several bordering structures, causing complications, like shunts between the aorta and auricles, and cardiac taponade among others.

Stents have great problems with the re-stenosis, the rupture of their structure, and all the negative effects in hemodynamics, such as losing a vessel's compliance and elasticity. The devices remain in place for extended periods of time in the heart. The devices can cause local inflammation and the long-term results are unknown. The devices can be corroded and/or migrate, producing future complications. An innumerate number of opened questions exist with regard to the effects that these devices produce in other diseases and how much they can affect the future diagnostic and therapeutic methods.

It would be useful to develop a new and improved self-piercing suture and method of using the same, wherein the suture effectively holds tissues together while not migrating in the tissue.

SUMMARY OF THE INVENTION

According to the present invention, there is provided a tissue fixation device includes a tack having at least two flexible arms on a first end of said anchor. A deployment device for deploying a tissue fixation device, wherein the deployment device is a deployment gun is also provided.

DESCRIPTION OF THE DRAWINGS

Other advantages of the present invention are readily appreciated as the same becomes better understood by reference to the following detailed description, when considered in connection with the accompanying drawings wherein:

FIG. 1 is a side view depicting a tissue tack partially extending outside a barrel of a deployment device;

FIG. 2 is a side view depicting a tissue tack partially extending outside a barrel of a deployment device;

FIGS. 3A-F are side views depicting how a deployment device deploys a tissue tack, wherein FIG. 3A depicts a side view partially cut away of the deployment device of the present invention, FIG. 3B depicts a top view partially cut away of the deployment device of the present invention showing the locking mechanism in a retracted position with the tissue tack still locked in place, FIG. 3C depicts a side view partially cut away of the deployment device of the present invention, FIG. 3D depicts a top view partially cut away of the deployment device of the present invention showing the locking mechanism in an extended position with the tissue tack still locked in place, FIG. 3E depicts a side view partially cut away of the deployment device of the present invention, FIG. 3F depicts a top view partially cut away of the deployment device of the present invention showing the locking mechanism after the tissue tack has been deployed;

FIG. 5 is a photograph of a tissue tack wrapped in copper wire for increasing visualization of the tissue tack;

FIG. 6 is a photograph showing an ultrasound image of unmodified (untreated, left) and modified (treated, right) tissue tacks;

FIGS. 8A-F are side views depicting three stages for deploying a tissue tack; FIGS. 8A and 8D show the tissue tack within the deployment device; FIGS. 8B and 8E show shows the deployed tissue tack; and FIGS. 8C and 8F show shows the deployed tissue tack within a body;

FIGS. 11 A-C are side views depicting an alternative embodiment of the deployment device of the present invention;

FIGS. 12 A-D are side views depicting a deployment device having a curvature;

FIGS. 13 A-C are side views depicting the lumen of the deployment device;

FIGS. 15A-D are side views depicting a locking mechanism of a deployment device;

FIGS. 26 A-H are side views showing an alternative manner in which a tissue defect is corrected using the tissue tacks of the present invention;

FIGS. 32 A-D are side views showing an alternative embodiment for the deployment device of the present invention including a curvature.

DETAILED DESCRIPTION OF THE INVENTION

Figure 4:
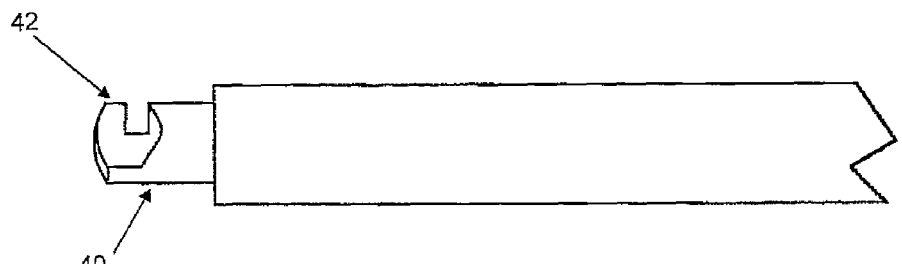
FIG. 4 is a are side view depicting a locking mechanism of a deployment device.
Figure 9A:
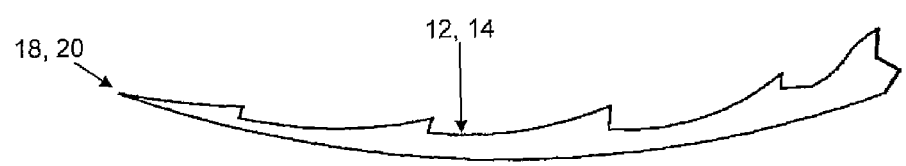
FIGS. 9A-D are side views depicting various embodiments for the exterior surface of the tissue tack.
Figure 9B:
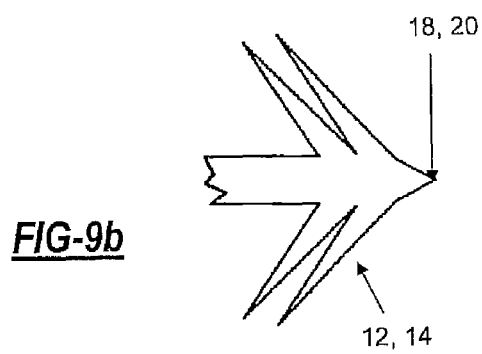
Figure 9C:
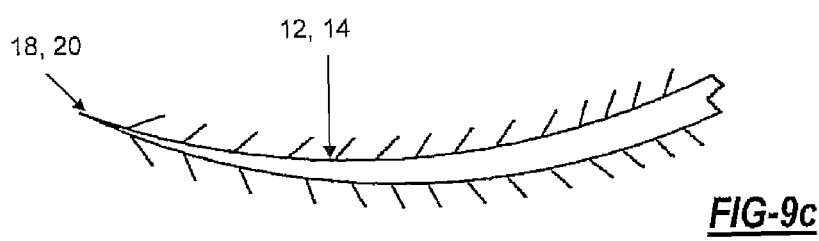
Figure 9D:
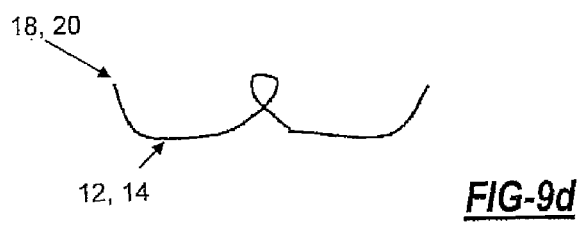
Figure 7A:
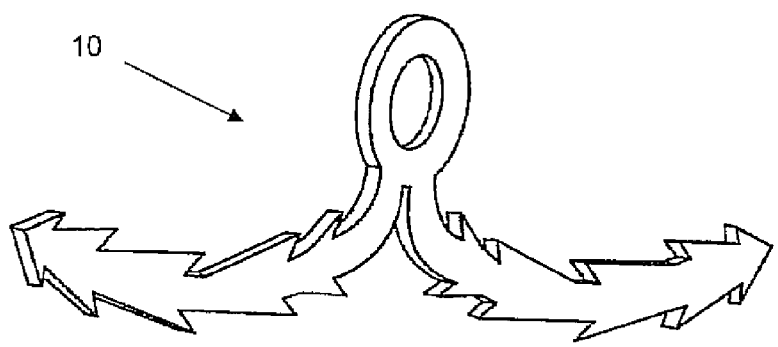
FIGS. 7A-F are side views depicting embodiments of the tissue tack of the present invention.
Figure 7B:
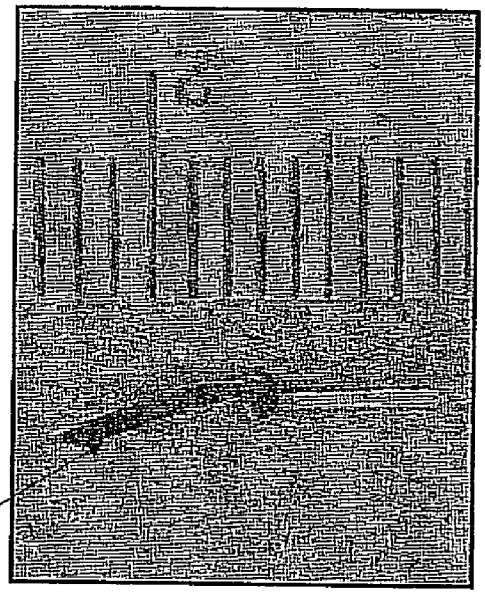
Figure 7C:
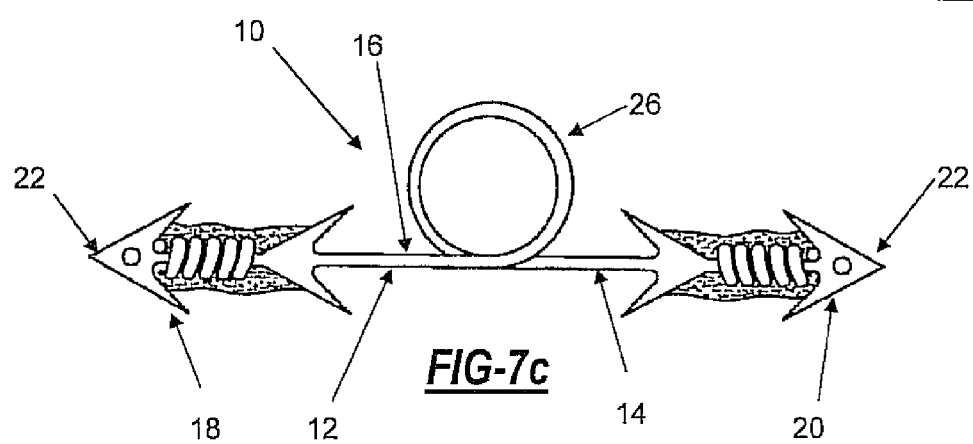
Figure 7D:
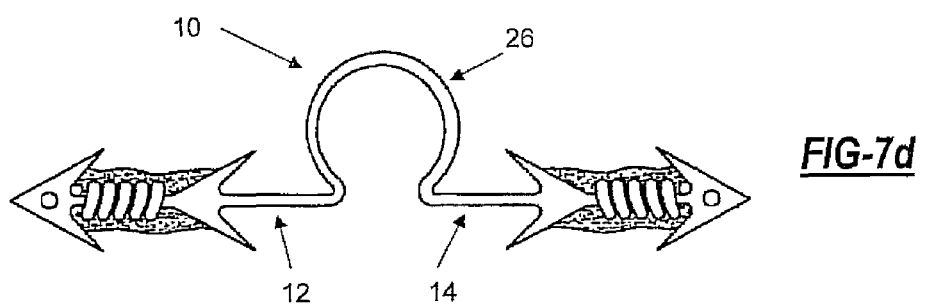
Figure 7E:
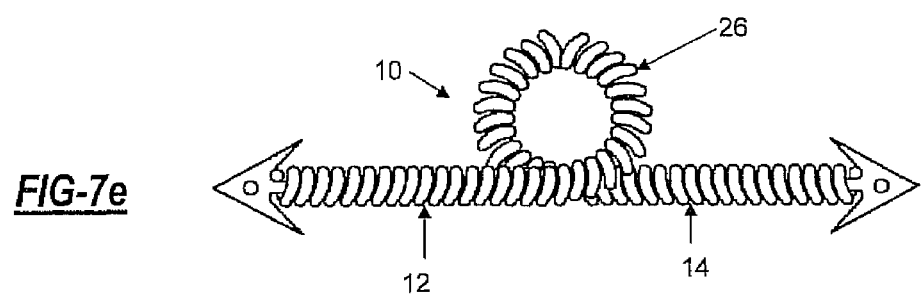
Figure 7F:
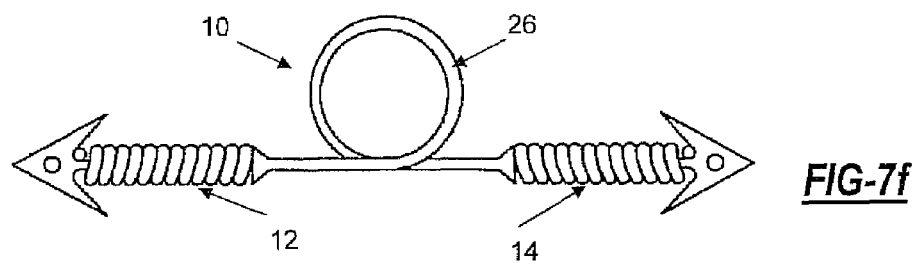
Figure 10A:
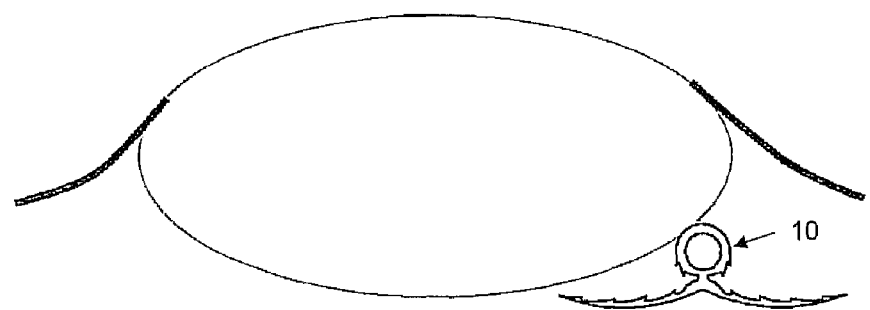
FIGS. 10A-C are side views depicting the manner in which two tissue tacks can be used in connection with one another.
Figure 10B:
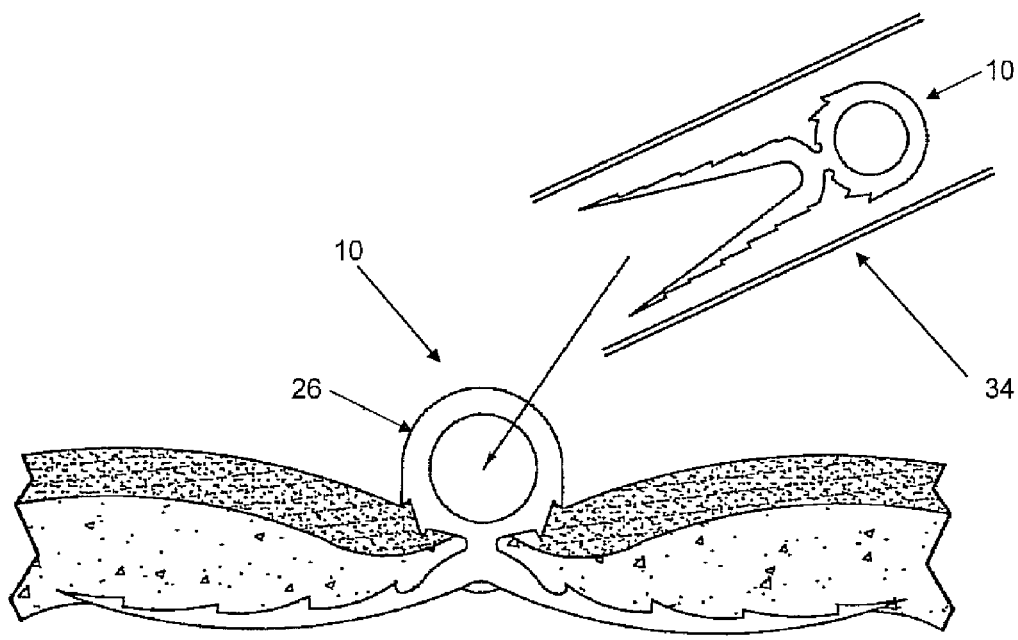
Figure 10C:
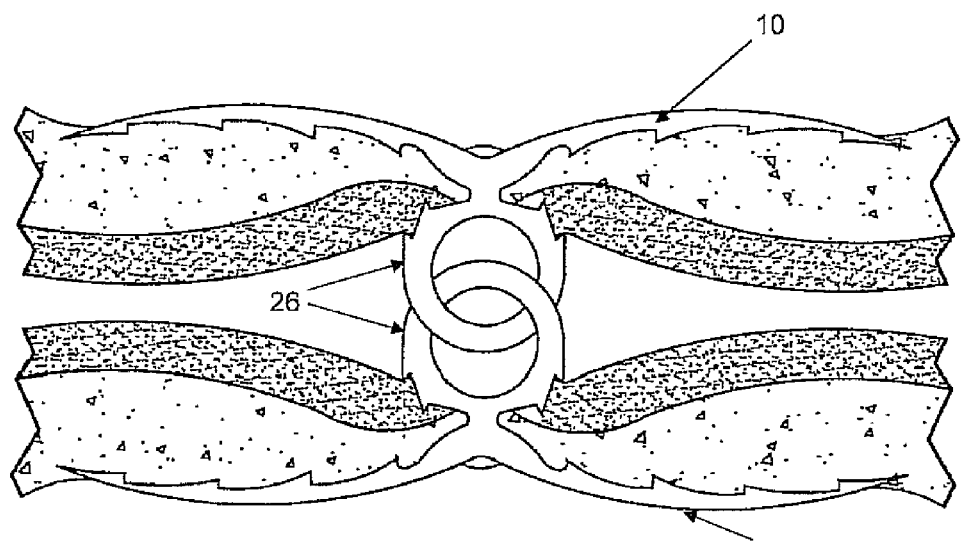
Figure 14C:
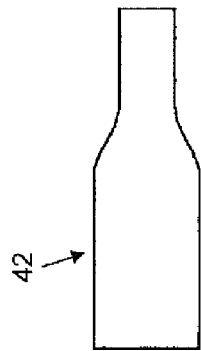
FIGS. 14A-D are side views depicting a locking mechanism of a deployment device.
Figure 14A:
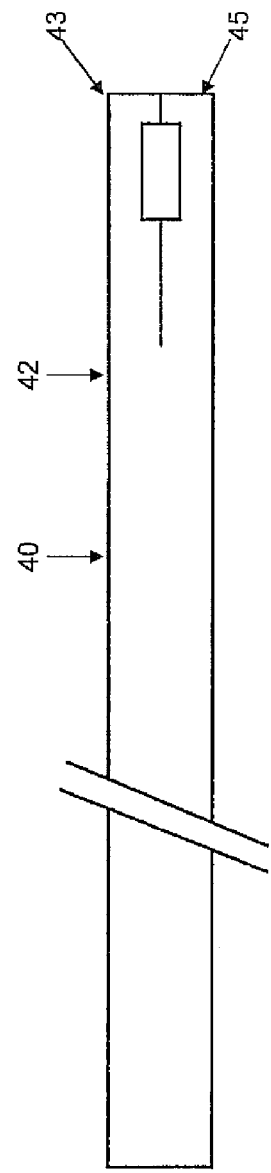
Figure 14D:
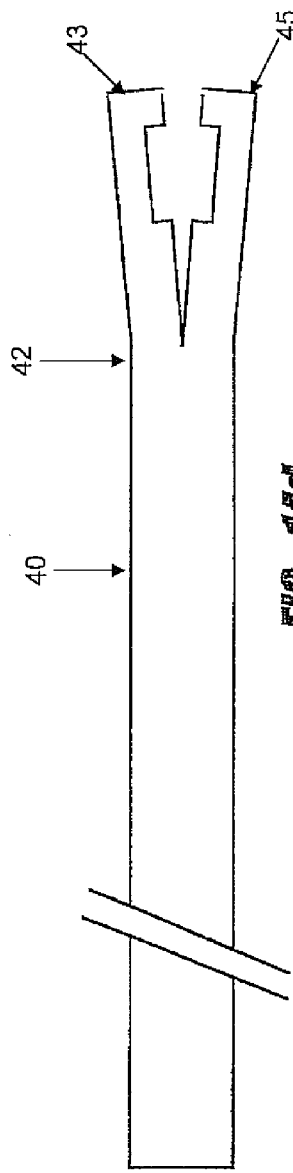
Figure 14B:
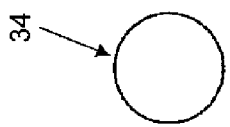
Figure 16A:
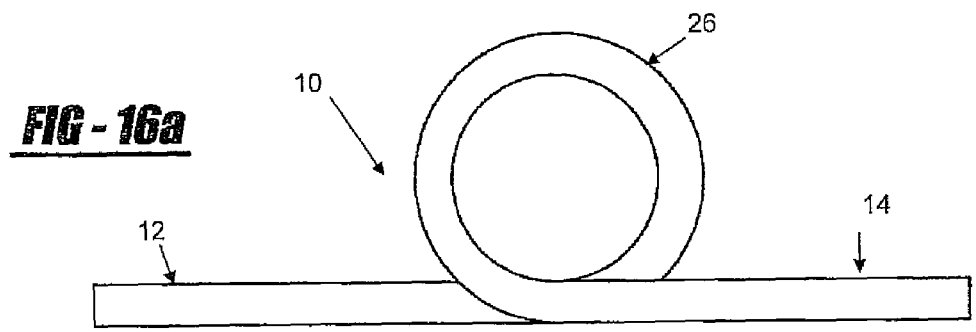
FIGS. 16 A-H are side views depicting alternatives for the anchoring device of the present invention.
Figure 16B:
Figure 16E:
Figure 16G:
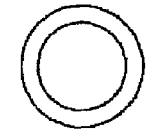
Figure 16C:
Figure 16F:
Figure 16H:
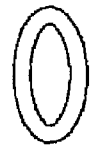
Figure 16D:
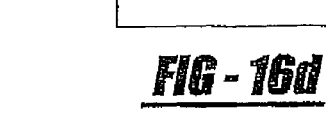
Figure 17:
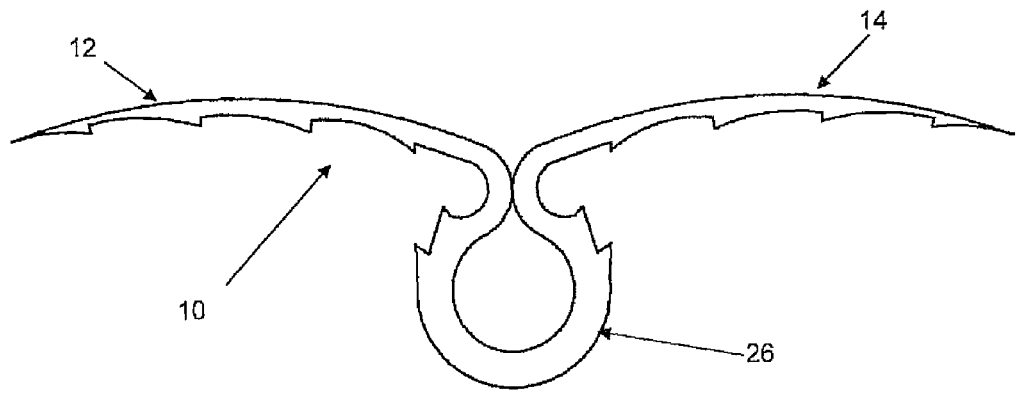
FIG. 17 is a side view showing an alternative embodiment of the tissue tack of the present invention.

The present invention provides an apparatus for use as a tissue fixation device. The tissue fixation device is a tissue tack made of biocompatible materials as generally shown at 10 in the Figures.

The term "tissue tack deployer" and "deployer" both refer to the apparatus used for deploying a tissue tack into tissue.

The term "hollow barrel" as used herein is equivalent to the term "barrel" in the present invention. A barrel is a hollow lumen in which the tissue tacks of the present invention are placed prior to deployment into the body of a patient.

The term "tissue" as used herein is meant to include, but is not limited to, an aggregation of morphologically similar cells and associated intercellular matter acting together to perform one or more specific functions in the body. Four basic types of tissues include muscle, nerve, epidermal, and connective tissues.

The tissue tack 10 of the present invention has a body portion 16 having at least two arms 12, 14 extending radially therefrom. The arms 12, 14 both can include puncturing ends 18, 20 to allow for entry of the tissue tack 10 into the tissue. Opposite the arms 12, 14 is an anchoring mechanism 26. An anchoring mechanism 26 extends from the body 16 of the device 10 in order to anchor the device 10 when disposed in the tissue. The anchoring mechanism 26 is flush with the tissue when the device 10 is in the tissue. Thus, the device 10 will not migrate into the tissue and discomfort to the patient is minimized. The body portion 16 as shown in the FIGURES, and especially in FIGS. 8A-8C, is very short in length compared to the anchoring mechanism 26 and the arms 12, 14, and therefore the anchoring mechanism 26 is able to be flush with the tissue. In other words, the body portion 16 is of the size to retain two otherwise unjoined pieces of tissue in engagement once the tissue tack is deployed within tissue.

Figure 28:
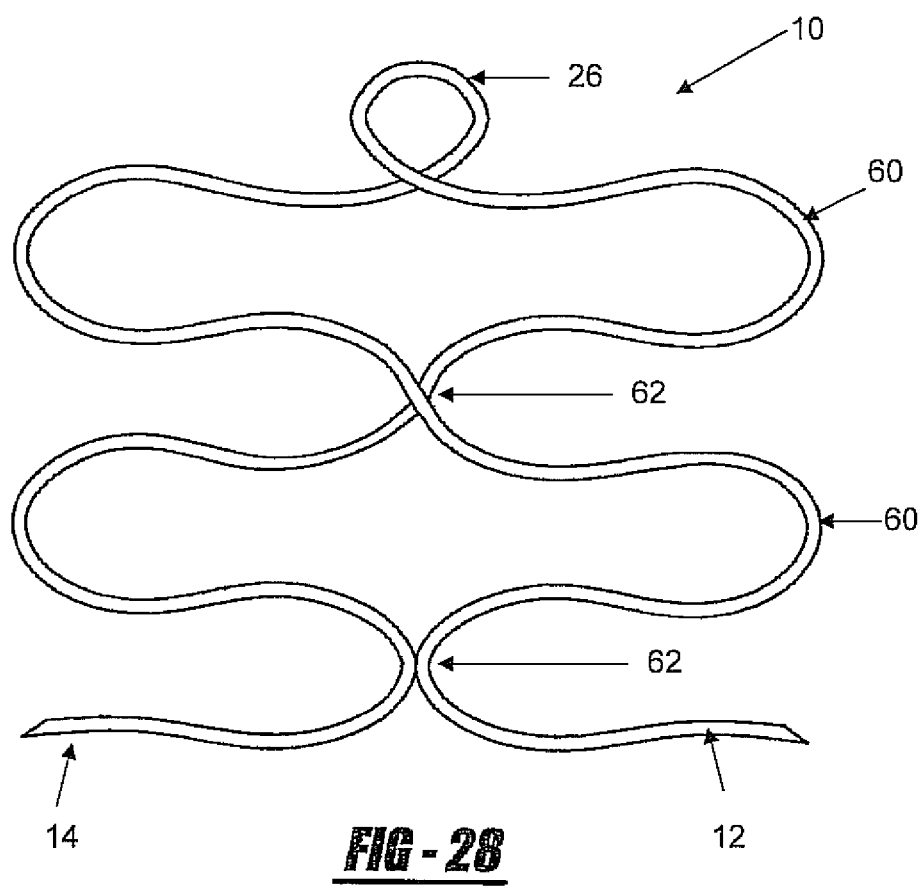
FIG. 28 is a side view showing an alternative embodiment of the tissue tack of the present invention.
Figure 29:
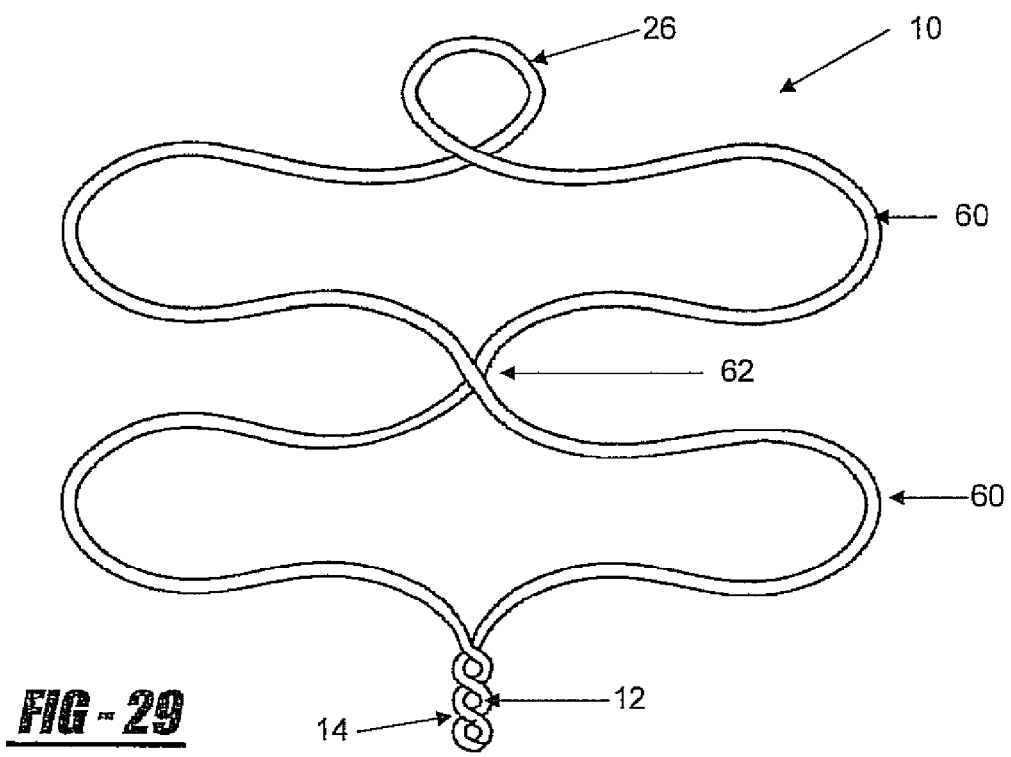
FIG. 29 is a side view showing an alternative embodiment of the tissue tack of the present invention.

The puncturing ends 18, 20 can be either an integral part of the tissue tack 10, or it can be a separate piece that is physically and/or chemically attached to the first end 16 of the tissue tack 10. The puncturing ends 18, 20 preferably include a pointed end portion 22 as in the embodiment of FIG. 1. In one embodiment, the pointed end portion 22 can be in the shape of a fishhook. The fishhook can serve to prevent the tissue tack 10 from migrating backwards and allowing the tissue to become unattached. Any other suitable pointed end portion 22 can be used. Examples of such end portions 22 are shown in FIGS. 9, 28, and 29, wherein the end portion 22 can include barbs, jagged edges or other tissue tack 10 retaining devices. The end portions 22 can also be beveled as shown in FIG. 9. Alternatively, the entire tissue tack 10 can include such barbs, jagged edges, or other retaining devices.

Preferably, the puncturing ends 18, 20 are made from the same biocompatible material as the tissue tack 10. Alternatively, the puncturing ends 18, 20 can be made of a different biocompatible material than the tissue tack 10 in order to enhance its puncturing capabilities. The puncturing ends 18, 20 can be manufactured separately than the tissue tack 10 if the puncturing ends 18, 20 are not an integral part of the tissue tack 10 using methods known to those of skill in the art.

The anchoring mechanism 26 is used to anchor the tissue tack 10 in the tissue and prevent migration. Without an anchoring mechanism, the tissue tack 10 is otherwise free to migrate further into the tissue, both after initial deployment and also during the time that the tissue tack 10 remains in the patient's body. This can cause physical pain to the patient and can also cause damage to the tissue.

The anchoring mechanism 26 can be an integral part of the tissue tack 10, or it can be physically and/or chemically attached at the body portion 16 of the tissue tack 10. Preferably, the anchoring mechanism 26 is a loop, from which the arms 12, 14 extend.

The anchoring mechanism 26 can also be used as a retaining portion. Preferably, the anchoring mechanism 26 is integral with the arms 12, 14; however, it can be a separate piece chemically and/or physically attached to the arms 12, 14 via the body portion 16. The anchoring mechanism 26 is used to keep the tissue tack 10 in position within a tissue tack deployer 30. It can be of any suitable shape to fit inside or outside the tissue tack deployer 30, but preferably in the shape of a loop or circle. Alternatively, the anchoring mechanism 26 can be shaped into a rectangular rather than circular wire as shown in FIG. 7, oval, or band-like (as shown in FIG. 16). By varying the rectangular shape with respect to the position of the arms 12, 14 of the tissue tack 10, this affects the strength of tissue grasping if the wider surface faces the anchoring mechanism 26 versus the narrower surface. Rectangular anchors also have a preferred orientation and resist rotation better than circular ones. Preferably, the anchoring mechanism 26 is made from the same biocompatible material as the tissue tack 10. Alternatively, the anchoring mechanism 26 can be made of different biocompatible materials than the tissue tack 10 in order to enhance anchoring and barrel-retaining capabilities. The anchoring mechanism 26 can be manufactured separately than the tissue tack 10 if it is not an integral part of the tissue tack 10. The manufacturing can be accomplished using methods known to those of skill in the art.

The tissue tack 10 can have modifications made to the exterior surface in order to enable the tissue tack to perform more effectively. For example, the tissue tack arms 12, 14 can be modified to improve tissue fixation and the arm 12, 14 and anchoring mechanism 26 can be modified to improve visibility by ultrasound and minimize ultrasound artifact and distortion of image. The modifications can be any modifications that improve the functionality of the tissue tack 10. Examples of such modifications include, but are not limited to, the addition of hooks, barbs, bristles and bends to the arms 12, 14 of the tissue tack 10 to improve tissue grasping and to increase the force required to remove the anchors (See FIGS. 9A-D).

The modifications can be made to improve tissue grasping capabilities and ease of removal.

Preferably, the tissue tack 10 is of a size relative to the incision in the tissue that is to be closed. Accordingly, the diameter of the arms and the total length of the tissue tack 10 can be selected to fit the incision. If the tissue tack 10 is being used to attach a periocardial patch in the heart, the size of the tissue tack 10 should be approximately 3 mm in diameter with an external length of 4 to 6 mm.

The tissue tack 10 is made of biocompatible materials. Whenever a foreign object is placed inside the body, rejection reactions can occur ranging from mild to severe irritation and inflammation, and even death. To keep rejection minimal, implants must be biocompatible. Preferably, the tissue tack 10 is made of stainless steel. Metals such as stainless steel, shape memory polymers, shape memory alloys, nitinol, titanium alloys, and cobalt alloys have high tensile, fatigue, and yield strengths, low reactivity and good ductility. A closely packed crystal structure and metallic bonding make metals and alloys useful in internal fixation devices. Alternatively, polymers such as polyethylene (PE) and hydrogels can be used. Depending on the processing methods, polyethylene can be made flexible and elastic, or hard and smooth. Biodegradable polymers could be used in cases where an incision in the tissue is expected to heal and become functional again. These polymers can degrade by hydrolytic instability, hydration, molecular backbone cleavage, loss of molecular weight, and solubilization. The degradation byproducts are removable by the body itself by natural functions such as phagocytosis. Sutures of this type eliminate the need for a second operation to remove them. Biodegradable polymers can be natural or synthetic. Some natural polymers include collagen, which already comprises about 30% of the protein in the body, chitosan, which is derived from a polysaccharide called chitin found in crustacean exoskeletons, and polyhydroxyalkanoates (PHA), which are secreted by certain species of microorganisms. Synthetic polymers include poly(glycolic acid) (PGA), which has been used in absorbable sutures, poly(lactic acid) (PLA), copolymers of PGA and PLA, and polydioxananone (PDS). Ceramics and glasses can also be used for the tissue tack 10. Composites of materials can be used to optimize strength and flexibility in the tissue tack 10, and one or more of the materials can be degradable to allow for tissue integration.

In forming the tissue tack 10, the tissue tack 10 can be laser cut from a band or cylinder of elastic material. The tissue tack 10 can also be formed using heat treatments or other methods known to those of skill in the art.

Further, the tissue tack 10 can be coated in an immunosuppressible material or other coating that limits the ability of the tissue or body within which the tissue tack 10 is being placed. Biologicals or chemicals can be incorporated on the surface of the tissue tack 10 that can be released or directly interact with surrounding tissue to modify tissue reactivity and promote or inhibit cell and extracellular matrix adhesion. Examples of such material include, but are not limited to, immunosuppressive compounds and agents. Immunosuppressive agents are defined as agents that suppress immune responses. The agents can include, but are not limited to, immunoprotective cells, such as Sertoli cells, stem cells, stem cell by-products, or other compounds that create an immunosuppressive effect. Examples of such immunosuppressive compounds include, but are not limited to, PKC inhibitors, glutamate receptor inhibitors, cyclosporins, FK506, corticosteroids, and ascomycins.

The tissue tack 10 can include an imageable material so that the location of the tissue tack 10 in the patient's body can be determined by imaging methods such as ultrasound, magnetic resonance imaging (MRI), computed tomography (CT), X-ray, fluoroscopy, nuclear imaging or any other imaging method known in the art. In order for a tissue tack 10 to be imageable in an X-ray visualization procedure, the tissue tack 10 must be more absorptive of the X-rays than the surrounding tissues. Radiopaque materials are commonly used such as stainless steel and nickel-titanium alloys. Radiopaque markers can also be used. In MRI, polymers are typically used. Any other suitable imaging material can be used. The tissue tack 10 can be made of a combination of imageable materials and other biocompatible materials or via a cover 11 formed of an imageable material that is placed about the tissue tack 10. Methods of manufacturing the tissue tack 10 from the materials above are well known in the art.

Figure 18A:
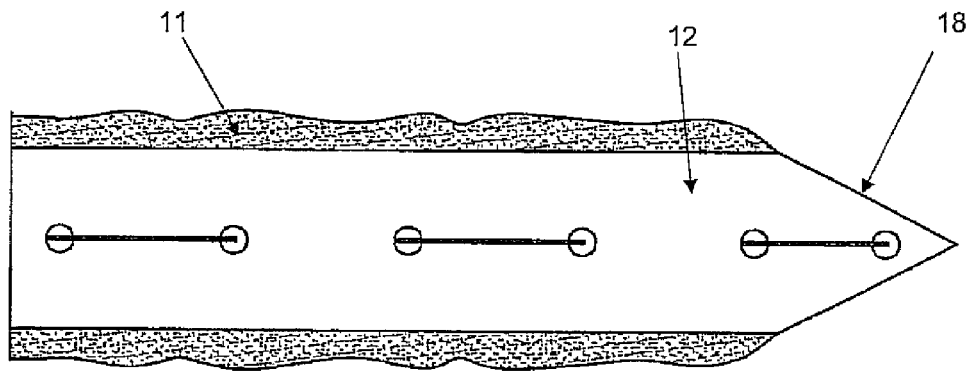
FIGS. 18 A and B are side views depicting arms of the tissue tack with polyurethane threaded therethrough and a coating of polyurethane over the barbed arms.
Figure 18B:
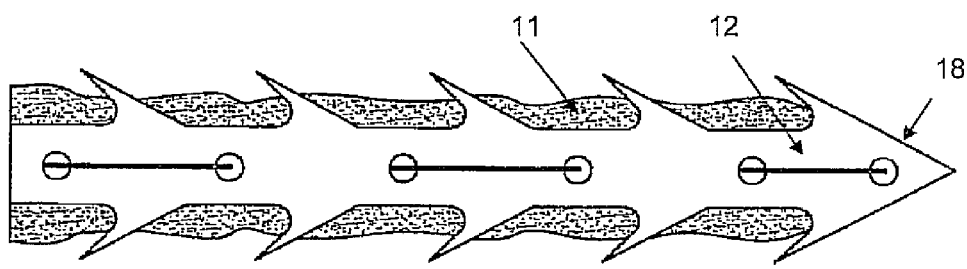
Figure 19A:
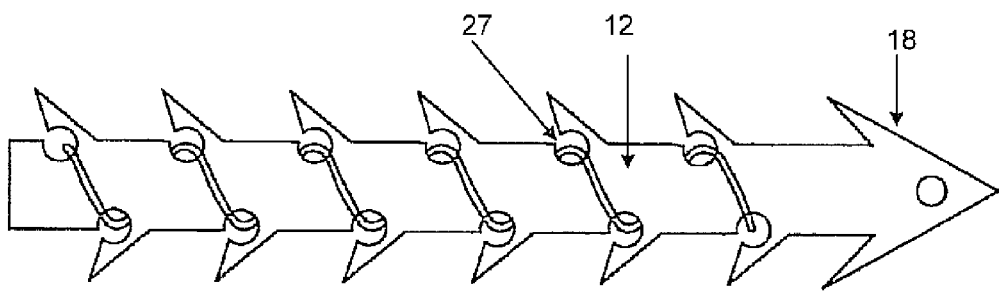
FIGS. 19 A and B are side views depicting arms of the tissue tack with polyurethane threaded therethrough.
Figure 19B:
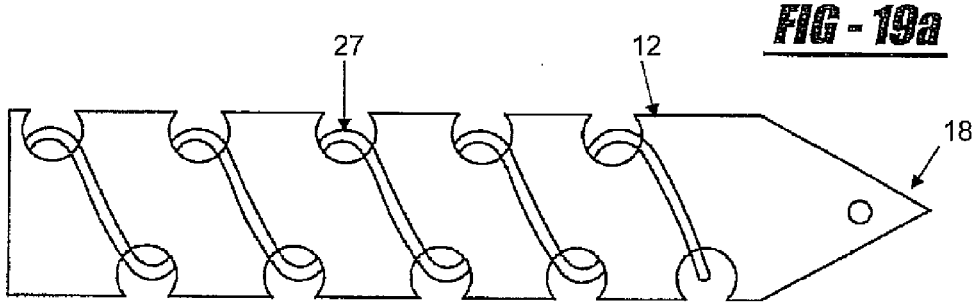
Figure 20A:
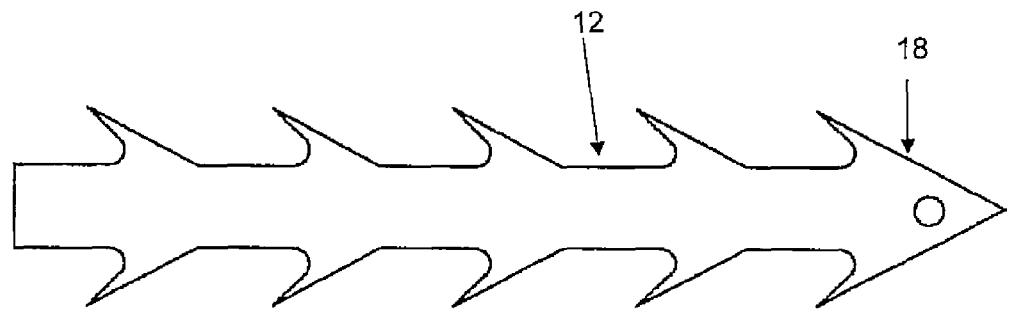
FIGS. 20 A and B are side views showing various embodiments for the exterior surface of the tissue tack.
Figure 20B:
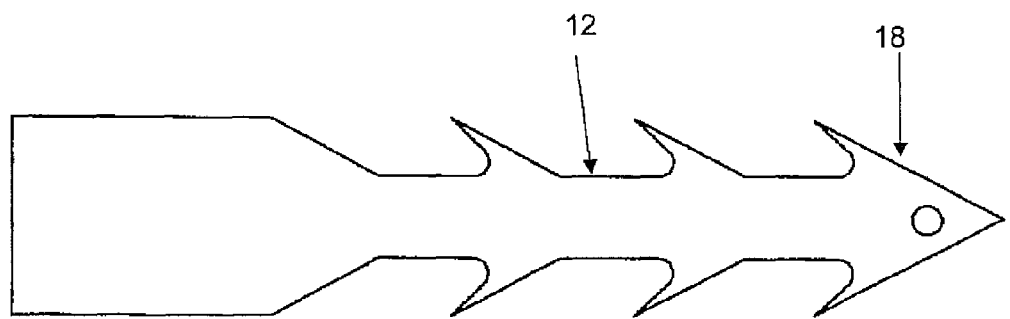
Figure 21A:
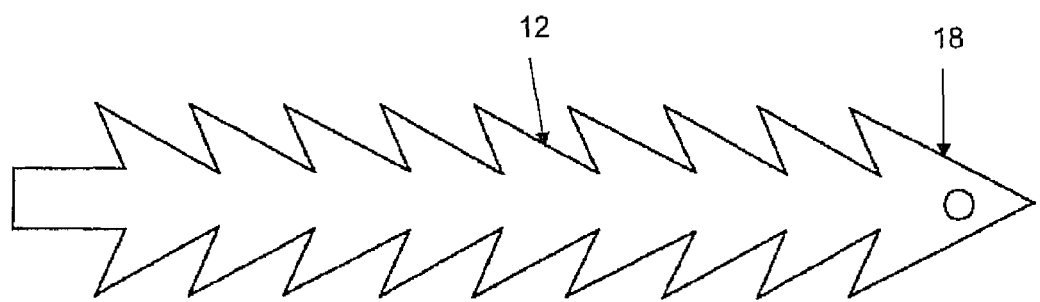
FIGS. 21 A and B are side views showing various embodiments for the exterior surface of the tissue tack.
Figure 21B:
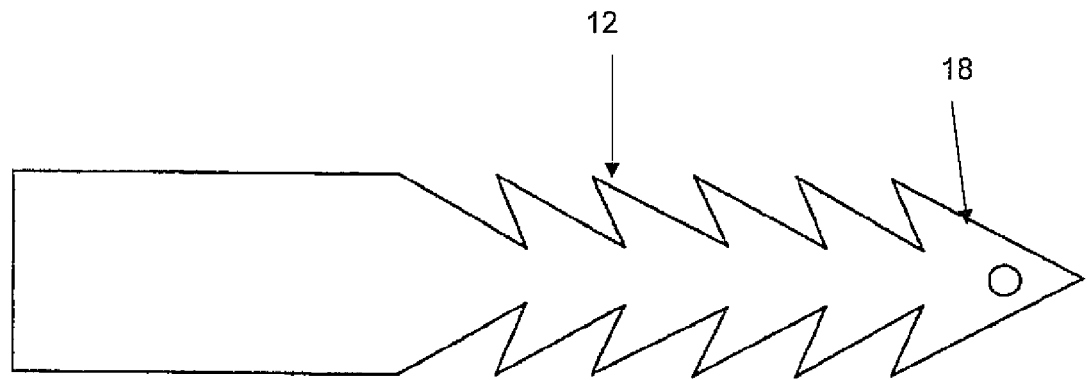
Figure 22A:
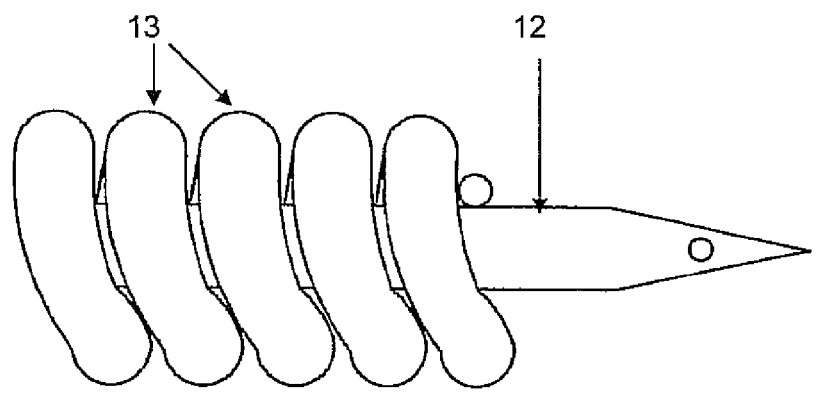
FIGS. 22 A-B are side views showing an alternative embodiment for the exterior surface of the tissue tack.
Figure 22B:
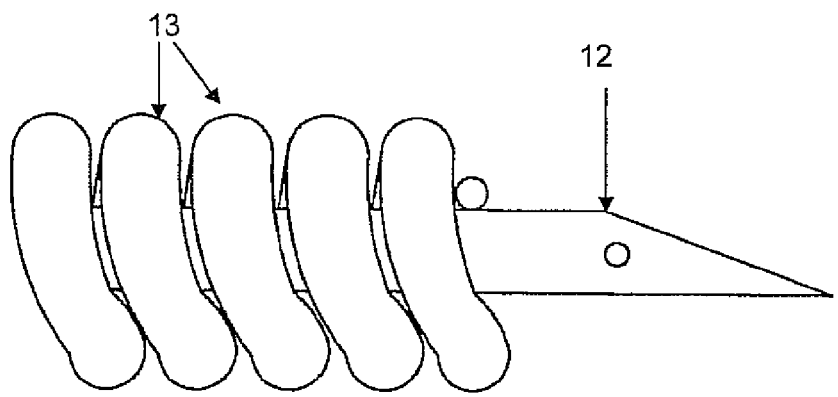
Figure 23A:
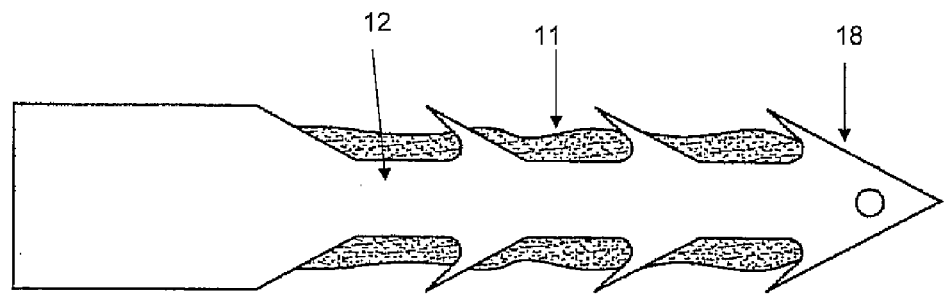
FIGS. 23 A-C are side views showing various embodiments for the exterior surface of the tissue tack.
Figure 23B:
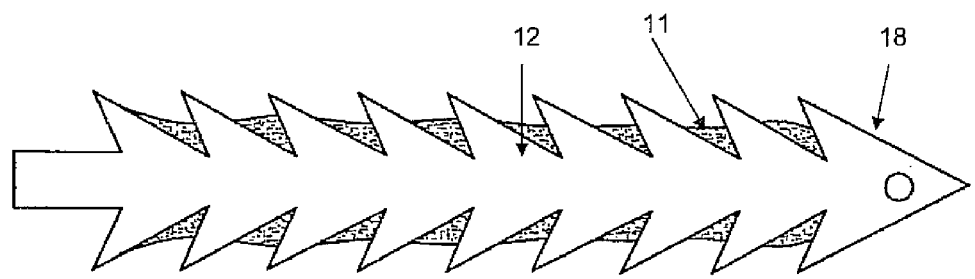
Figure 23C:
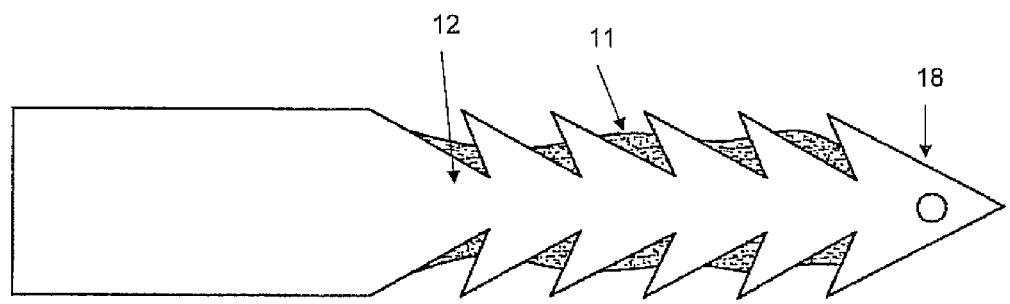

Alternatively, the tissue tack 10 can include physical modifications to better enable the tissue tack 10 to be visualized. This is accomplished by provide the best visualization of the arms 12,14 using ultrasound imaging at all incident angles, which is independent of the direction of the ultrasound beam. The modification also minimizes artifacts formed when the ultrasound beam strikes the arms 12,14. The modification can be accomplished via a diffusive surface modification or coating examples of which include, but are not limited to, wrapping a wire around the arms 12,14 or creating channels on the arms 12,14 to improve visualization. FIG. 5 shows a tissue tack 10 wherein the arms 12,14 are wrapped in copper wire 27 to improve visualization. The same effect can be achieved by cutting grooves, either linear or spiral, into the arms 12,14. The grooves can be cut using any mechanisms known to those of skill in the art. The mechanisms can include, but are not limited to, lasers and etching. The tissue tack 10 can also include coils 13 made of nitinol, or other similar materials, to aid in the visibility of the tissue tack 10. The coils 13 should be coiled loosely enough to enhance the visibility of the tissue tack 10. The surface can also be made smoother via a coating including polyurethane foam or other similar compound (see FIG. 18). Such a coating enables easier removal of the tissue tack 10, should removal become necessary.

The above types of modifications can be combined depending on the needs or circumstances. For example, for some applications such as ASD patch fixation, visibility of the anchors with minimal distortion is desired. Whereas for mitral ring fixation, strength of tissue grasping is of greater importance due to the forces being applied on the ring and anchors. A combination of modifications can be used in different parts of the same anchor. For example, barbed arms 12,14 can be combined with a spiral wound wire or groove on the anchoring mechanism 26. The design provides strength of tissue grasping while making the anchoring mechanism 26 of the tissue tack 10 more visible for navigating instruments to the tissue tack 10 or determining how many tissue tacks 10 have been deployed and in what location.

Also according to the present invention, a tissue tack deployer 30 is provided as shown generally in FIG. 2. The deployer 30 includes a housing 32 having a hollow barrel 34 connected thereto and a handle 36. The barrel 34 includes a spring loaded trigger 38 and a locking mechanism 40 on an end 41 of the barrel 34. The barrel 34 can include a curved extension 35, as shown in FIGS. 12 and 31-33. The curved extension 35 can be preset or can be steered depending upon the materials used. Preferably, the curved extension 35 is preset such that upon extending the curved extension 35 from the barrel 34 the curved extension 35 curves pursuant to the preset limitations. Alternatively, the curved extension 35 can include a curving mechanism for altering the degree of curvature, using steering mechanisms known to those of skill in the art. The locking mechanism 40 maintains the tissue tacks 10 that are mounted in the barrel 34 and allows the tissue tacks 10 to travel along the barrel 34. Finally, the locking mechanism 40 has a tip 42, as shown in FIGS. 4, 11, 14 and 15, for both holding the tissue tack 10 in place and releasing the tissue tack 10 when in the desired location. The tip 42 can have a hook, gripper, key lock, or other similar design. The tip 42 can be formed from as few as one part or multiple parts 43,45 (as shown in FIGS. 14 and 15). When multiple parts 43,45 are utilized, the parts 43,45 converge to maintain the tissue tack 10 within an opening 47 in the parts 43,45. The parts 43,45 are maintained in a closed position by the barrel 34 of the deployer 30, therefore when the tip 42 is extended from the barrel 34, the parts 43,45 are no longer held together and the tissue tack 10 can be released. Alternatively, the tip 34 can include a mechanism for locking/closing the parts of the tip 42, which can be released upon deployment of the tissue tack 10.

FIG. 11 shows a guide 52 located on the end of the tip 34. The guide 52 includes a male portion 54 that mates with a female guide portion 56 present on a patch previously deployed, such that the male portion 54 can align with the female portion 56 to ensure that the tissue tack 10 is deployed in the appropriate position. In other words, the deployer guide 52 functions as a key that must fit into a keyhole prior to deployment of the tissue tack 10. The system enables the surgeon to confirm that the appropriate number of tissue tacks 10 have been deployed and that the tissue tacks 10 have been deployed in the appropriate locations, without having to rely on additional imaging devices. The system also prevents a tissue tack 10 from being deployed too close to an edge of the patch that the tissue tack 10 is affixing. The tip 42 is designed to maintain the tissue tack 10 in place prior to deployment. Further, the tip 42 can be used to removing the tissue tack 10 by grasping, snaring, or hooking the tissue tack 10 and thereby removing the tissue tack 10.

Alternative embodiments of the tissue tack deployer 30 are shown in FIGS. 12 and 13. The deployer 30 can include lumens 58 that enable insertion of additional instruments for use at the site of deployer 30 insertion. For example, the lumen 58 enable the insertion of a light, vacuum, optics, a patch deployment device, or other devices that can be used in conjunction with the deployer 30 of the present invention. Typically, any device that can be used during a laparoscopic or endoscopic procedure can be used with the deployer 30 of the present invention. The device can also utilize real-time 3D echocardiography (RT3DE) via the above lumen 58. For RT3DE to be utilized it is preferable that an X4 matrix transducer on a SONOS 7500 system.

The deployer 30 includes a spring loaded trigger 38 able to actuate the motion of the tissue tack 10. The trigger 38 can be pulled by the finger of an operator. Inside the housing 32, the trigger 38 is connected to a spring-loaded drive mechanism that pushes the tissue tack 10 out of the barrel 34 causing the device 10 to be deployed into the tissue of the patient. The trigger 38 can be in any other suitable form. A handle 36 can also be attached to the housing 32 to ease in the operation and handling of the deployer 30.

An alternative embodiment of the deployer 30' is shown in FIGS. 31 and 31. The deployer 30' can include a pressure trigger 38' that is able to actuate the motion of the tissue tack 10 as shown in FIG. 33. The trigger 38' includes a handle having two arms 49,51 formed into a V-shape such that the bottom of the V 53 is distal to the barrel 34 and the two arms 49,51 of the handle support the pressure trigger 38' therebetween. The bottom of the V 53 contains a hinge 55 that connects the two arms 49,51. The trigger 38' includes a pressure gauge 57 that can be actuated by moving the two arms 49,51 of the handle together. The closer the two arms 49,51 are brought to one another, the higher the pressure. The pressure gauge 57 is matingly attached to the barrel 34 via a female nut 59, which engages and maintains the barrel 34 in place. The pressure gauge 57 can be actuated to a predetermined pressure, thereby ensuring that enough pressure is used to deploy the tissue tack 10. The pressure gauge 57 can also include a release valve 61 that enables pressure to be released from the deployer 30' if too much pressure is present.

It is advantageous to be able to deploy multiple tissue tacks 10 when there is either a large area to be sutured, or when there are multiple sites to be sutured. A mounting member 44 in the barrel 34 aids in mounting the tissue tacks 10. The mounting member 44 includes a guide mechanism 46, which guides the tissue tacks 10 that are mounted on the barrel 34. The guide mechanism 46 allows the tissue tack 10 to move both linearly along the barrel 34 and in a spiraling manner simultaneously during entry into the tissue. The guide mechanism 46 can include an open end 48 and a slot 50 that runs along a length of the barrel 34 in order to accommodate the arms 12,14 of the tissue tack 10. The tissue tacks 10 can be seated on to the barrel 34 in numerous manners known to those of skill in the art. The tissue tack 10 can also be situated in any other suitable manner on the barrel 34.

Figure 30:
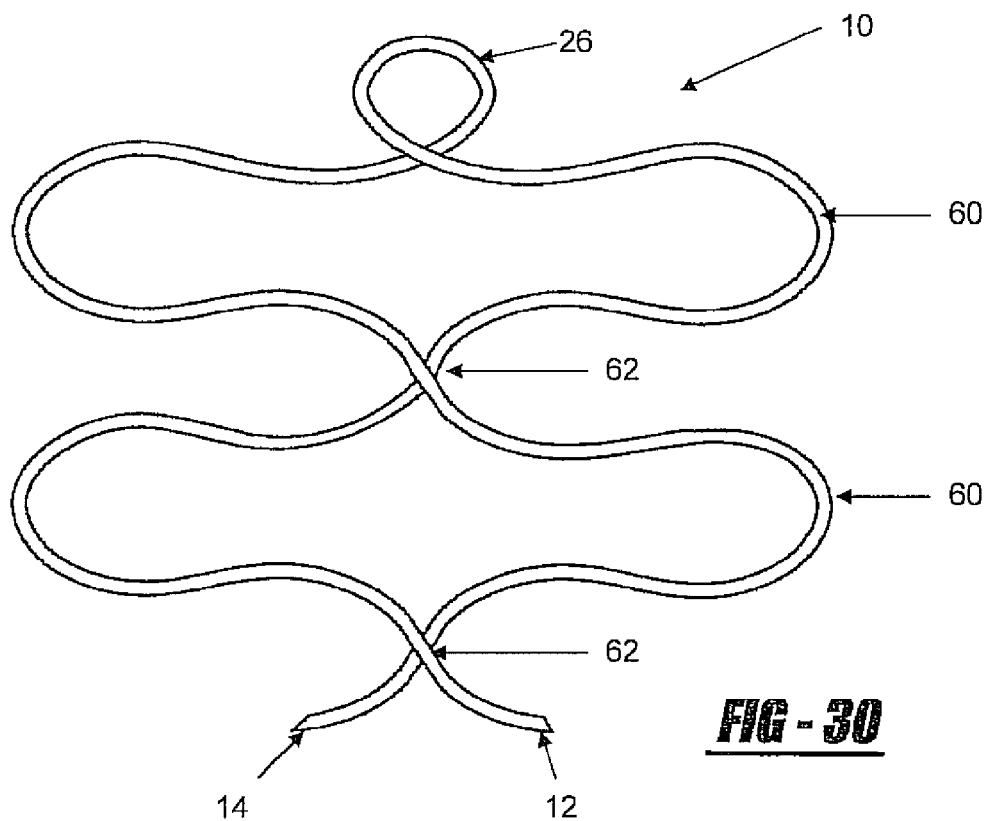
FIG. 30 is a side view showing an alternative embodiment of the tissue tack of the present invention.
Figure 31A:
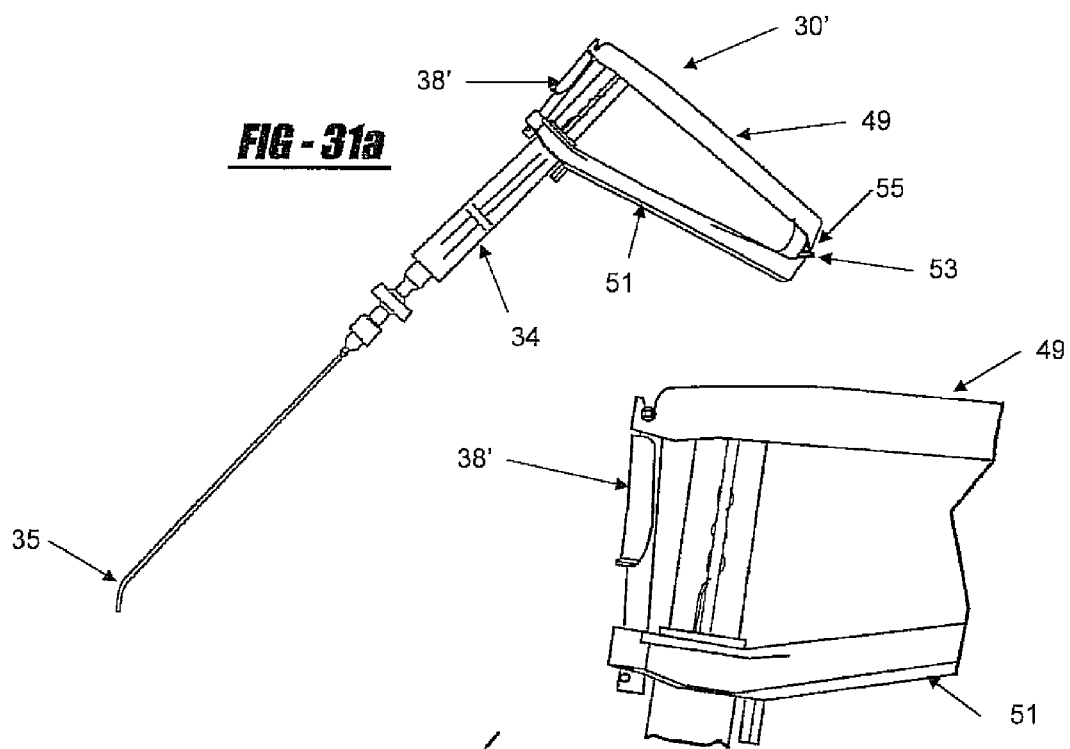
FIGS. 31 A-D are side views showing an alternative embodiment for the deployment device of the present invention including a curvature.
Figure 31B:
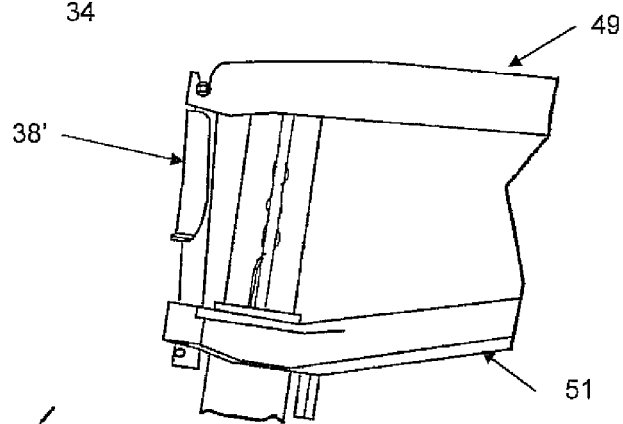
Figure 31D:
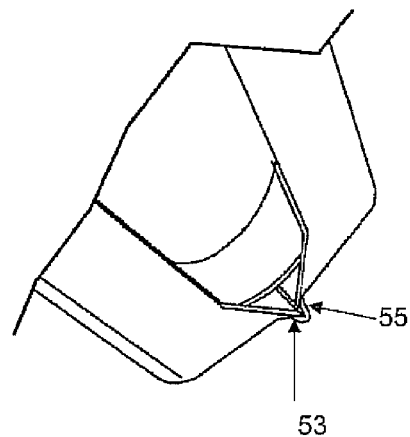
Figure 31C:
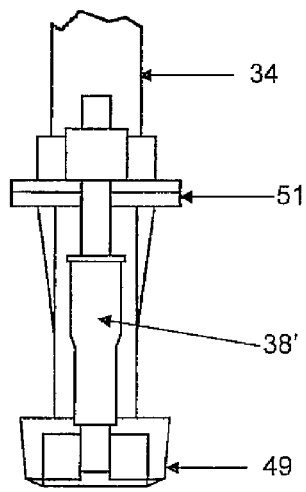
Figure 33A:
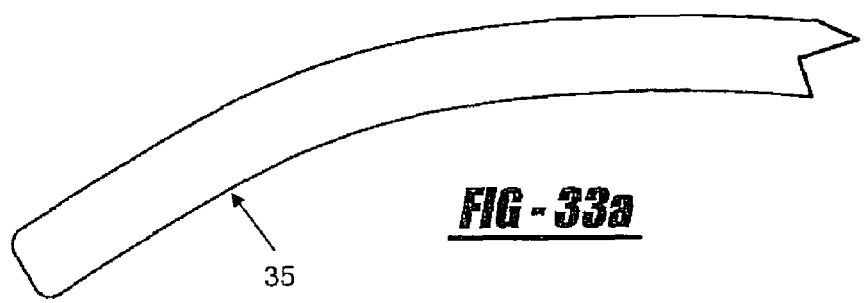
FIGS. 33 A-I are side views showing a tissue tack being deployed from the deployment device shown in FIGS. 31 and 32.
Figure 33B:
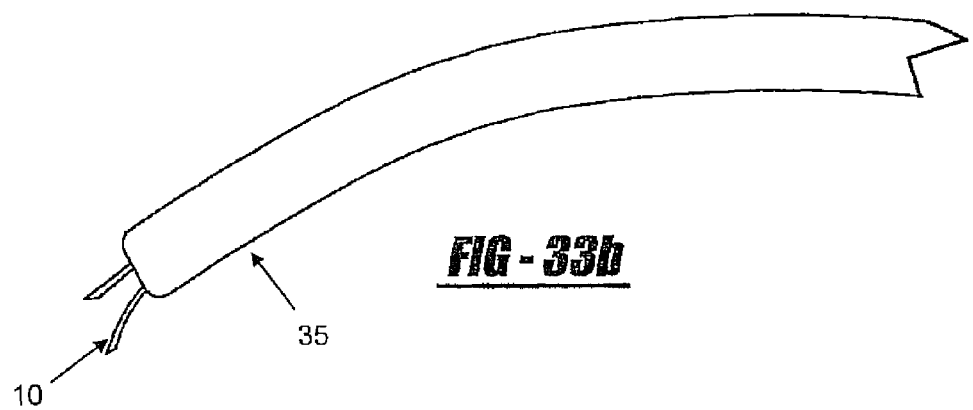
Figure 33C:
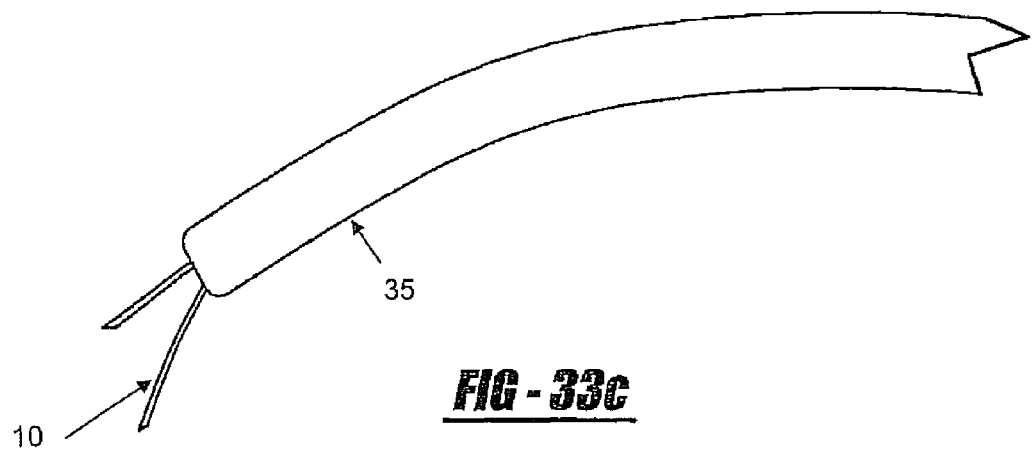
Figure 33D:
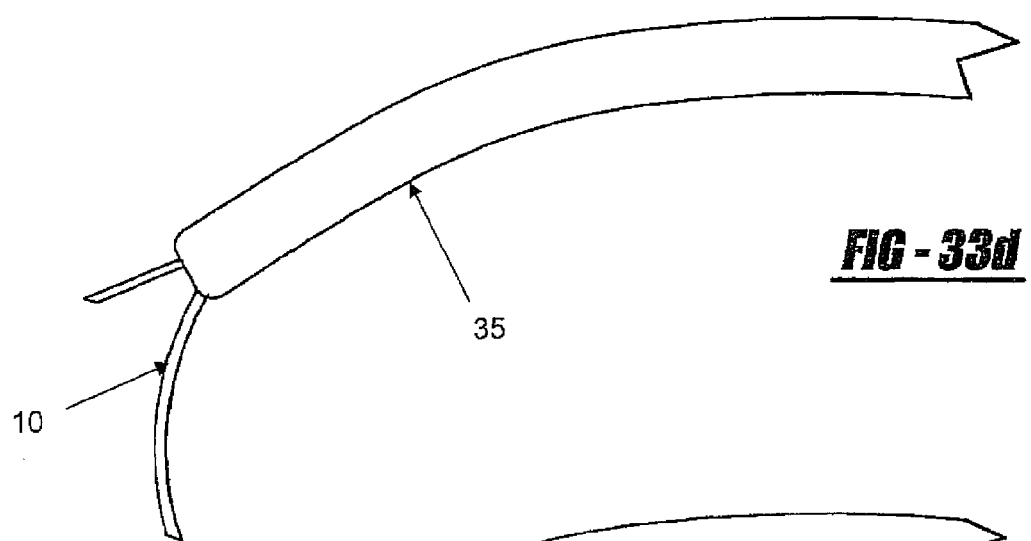
Figure 33E:
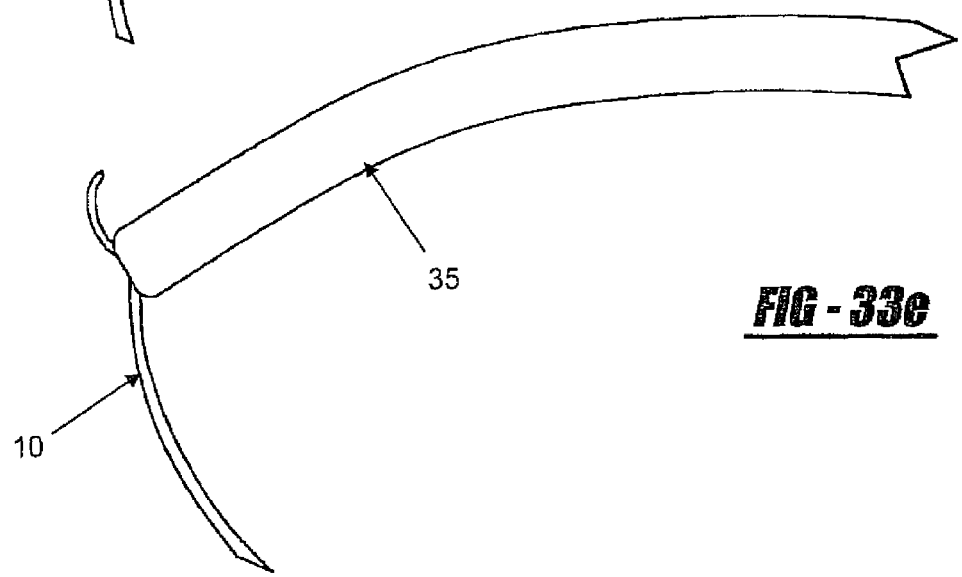
Figure 33F:
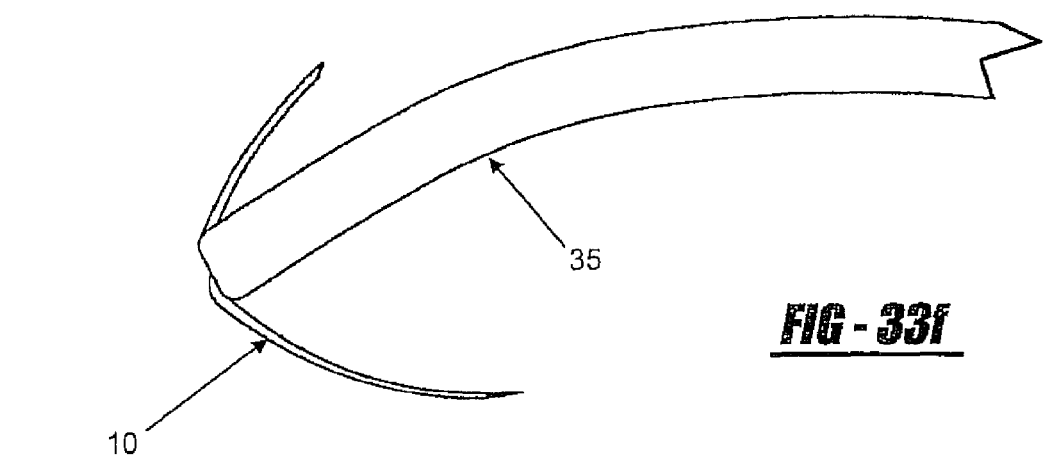
Figure 33G:
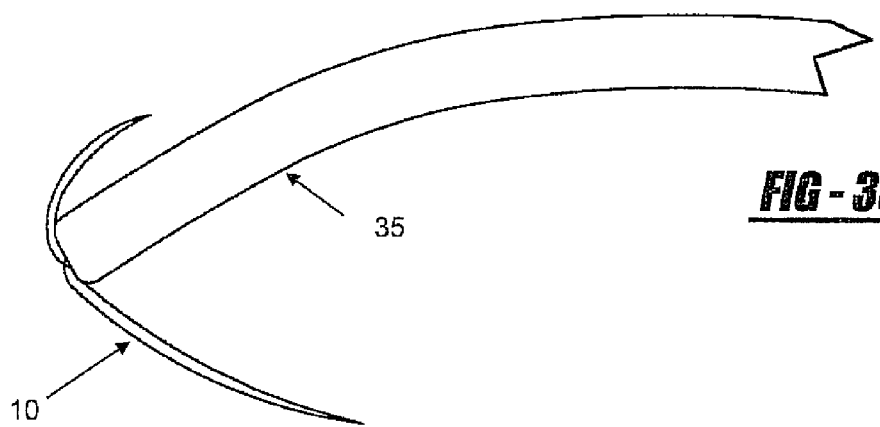
Figure 33H:
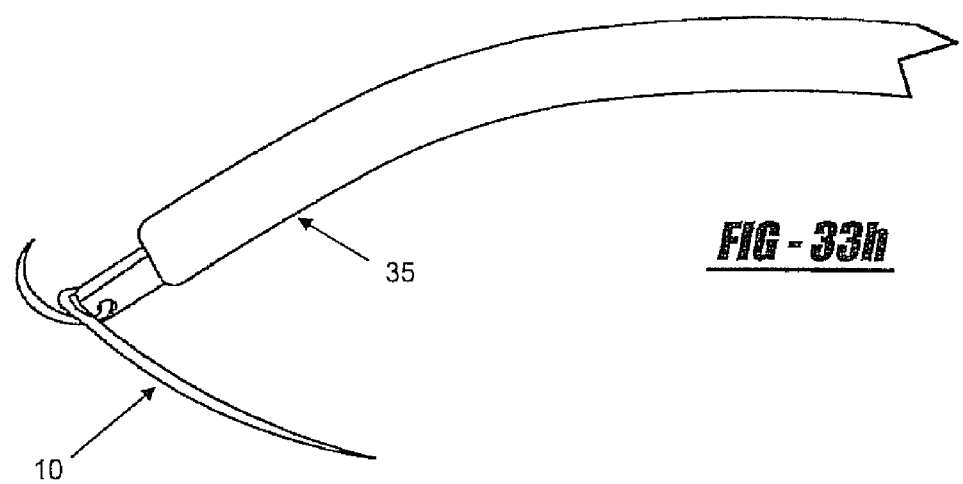
Figure 33I:
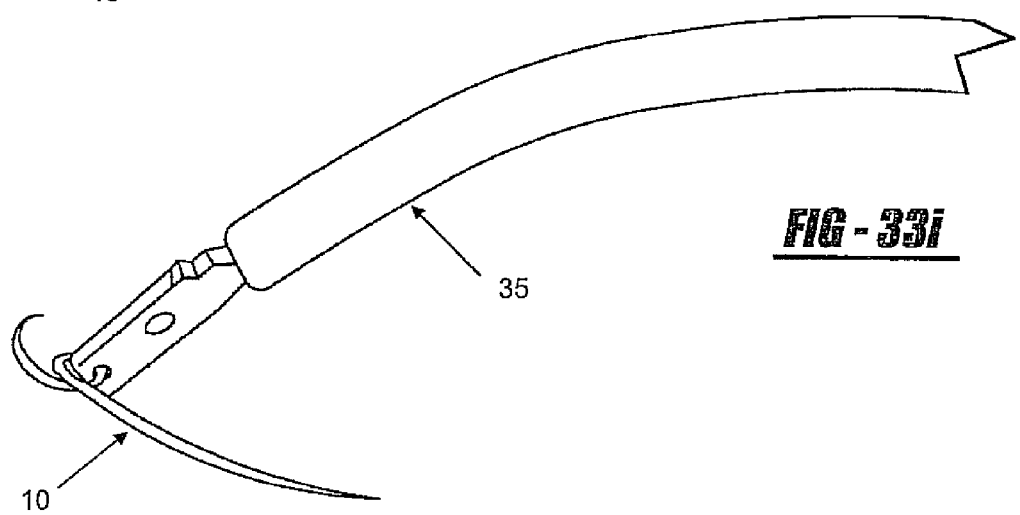

The tissue tack 10 of the present invention is preferably used to interconnect a patient's tissue together. For example, the tissue can be heart tissue, muscle tissue, or vascular tissue. Alternatively, the tissue tack 10 can be used to connect tissues in any suitable site in the body. For example, the tissue tacks 10 shown in FIGS. 28-30 have a modified anchoring mechanism 26, such that the anchoring mechanism 26 is twisted to create at least one tissue separating device 60 with at least one tissue separation spaces 62 that enables a single tissue tack 10 to be used to affix multiple layers of tissue. The twisting of the anchoring mechanism 26 creates a small generally circular anchoring mechanism 26 and a larger, generally oval-shaped, tissue separating device 60, as shown in FIGS. 28-30. Therefore, when the tissue tack 10 is deployed into layers of tissue, the tissue separating device 60 maintains a distance between layers by keeping the layers of tissue in tissue separation spaces 62. Multiple tissue separation devices 60 can be included in a single tissue tack 10.

The tissue that is being connected can be two opposing sides of an incision. It can also be a native piece of tissue and a graft or prosthesis to be attached to that native piece of tissue. Examples of such closures include, but are not limited to, the fixation of a patch to tissue for closure of atrial septal defect, ventricular septal defect, orifice or opening into a vessel or aneurysm (out pouching) in the heart or blood vessel, fixation of two tissue layers together such as two edges of a blood vessel or valve leaflet, vessel to vessel anastomosis, vessel to synthetic tube graft anastomosis, and approximation of tissue under tension by a process of interlocking two tissue tacks 10 that are attached to separate tissue layers. Additionally, the tissue tack 10 can be used to comply and fix to a predetermined position next to another system or catheter, for cuffing, suturing, monitorization of pressure, thermal, electrocardiographical, or of electrophisiological ablation or the device can have in its distal end one or more sensorial and transmissioner ends: thermal, magnetics, echographics, radio frequency, radar and others, that allows determining its location in a tridimensional field, echographic, radiologic, magnetic, of radio frequency, thermal or by radar. The tissue tack can also be used to close cardiac atrial appendix by anchors, to close PFO, to close ASD, to close VSD, to reduce the mitral ring, to fix two valves of a cardiac valve through its distal end, to close any orifice by means of anchors with or without an additional weave, to fix the aneurism of a VSD by means of an anchor to close the same one, to introduce one patch through the aorta pulling back and to introduce the system of anchors by the end of the heart, to fix patch from the right ventricle.

The present invention provides a method of suturing the tissue with the tissue tack 10 by puncturing the tissue of a patient to allow entry of the tissue tack 10 into the tissue. The tissue tack 10 is flushly anchored in the tissue so that the tissue is effectively held together. The method can also include, prior to the puncturing step, a step of deploying the tissue tack 10 through an incision in the tissue in order to suture the tissue. The deploying step is accomplished by inserting a tissue tack deployer 30 into an incision, and then guiding the deployer 30 to the site in need of suturing. The deployer 30 can also be inserted into a trocar that is disposed through the incision. A trocar can be used in such operations as a cardiovascular operation. The deployer 30 can be guided to the suture site by using an imaging method such as ultrasound, MRI, CT, X-ray, fluoroscopy, or nuclear imaging.

Prior to entry into the tissue, the arms 12,14 of the tissue tack 10 are straightened and forced together, in parallel, within a deployment device. The tissue tack 10 enters the tissue and the arms 12,14 open and extend in opposite directions, as shown in FIG. 2. The anchoring mechanism 26 can be folded to limit the size of the tissue tack 10 prior to deployment. The folding is similar to what occurs with the arms 12,14, wherein the anchoring mechanism 26 is deformed into a straightened position to limit the size of the tissue tack 10 within the deployer 30.

The deployer 30 is used to insert the tissue tacks 10 into the patient's tissue. In a preferred embodiment, the tissue tack deployer 30 is in the shape of a gun. Any other suitable shape can also be used. In general, the deployer 30 is of a small size. It can be produced by any method known to those of skill in the art for forming a deployer 30 as disclosed above. The entire deployer 30 or individual parts can be made of any suitable materials such as metals, plastics, ceramics, and composites. The deployer 30 can be used during macrosurgery and microsurgery procedures. A computer can be used to control the deployer 30. Also, a robot can be used to move and manipulate the deployer 30. The housing 32 is the base for the deployer 28 upon which other elements are connected. A hollow barrel 34 is operatively connected to the housing 32. The tissue tacks 10 rest in the barrel 34 prior to deployment into tissue. The diameter of the barrel 34 is such that it can accommodate the diameter of tissue tack 10 required for the suture. The length of the barrel 34 is such that it can accommodate the length of the tissue tack 10 required for the suture. The length of the barrel 34 can also be extended so that a plurality of tissue tacks 10 can be loaded within the deployer 28. The barrel 34 should be able to fit though a trocar and cannula if they are used in the operating procedure.

A method of deploying a tissue tack 10 into tissue is provided. This is accomplished by loading a device 10 onto the barrel 34 of the deployer 30, inserting the barrel 34 through an incision of the patient and into the tissue, guiding an end of the barrel 34 to the site to be sutured, and finally driving the device 10 off of the barrel 34 and into the tissue at the suture site. Alternatively, instead of one tissue tack 10 loaded onto the barrel, a plurality of tissue tacks 10 can be loaded. The tissue tack 10 is loaded so that the tissue tack 10 sits inside the barrel 34, and the arms 12,14 of the tissue tack 10 projects outside of the barrel 34. Any other suitable method to load the tissue tack 10 can be performed without departing from the spirit of the present invention.

The barrel 34 can be inserted in a trocar disposed in the incision of a patient. The end of the barrel 34 can be imaged while it is in the tissue in order to guide the barrel 34 to the suture site. This can be accomplished by an imaging method such as ultrasound, MRI, CT, X-ray, fluoroscopy, or nuclear imaging. Any other suitable imaging method known to those of skill in the art can also be used. The tissue tack 10 can be driven off of the barrel 34 by any other suitable method.

When inserting multiple tissue tacks 16, the deployer functions by placing the first tissue tack 10 in place. Then, a second tissue tack 10 can be threaded through the first tissue tack 10 and is then deployed on an opposite side of the tissue. Once the second tissue tack 10 is released, the two edges of the tissue pull together. The process is repeated with numerous tissue tacks 10 until the edges of the tissue are pulled together (see FIG. 26).

Figure 24A:
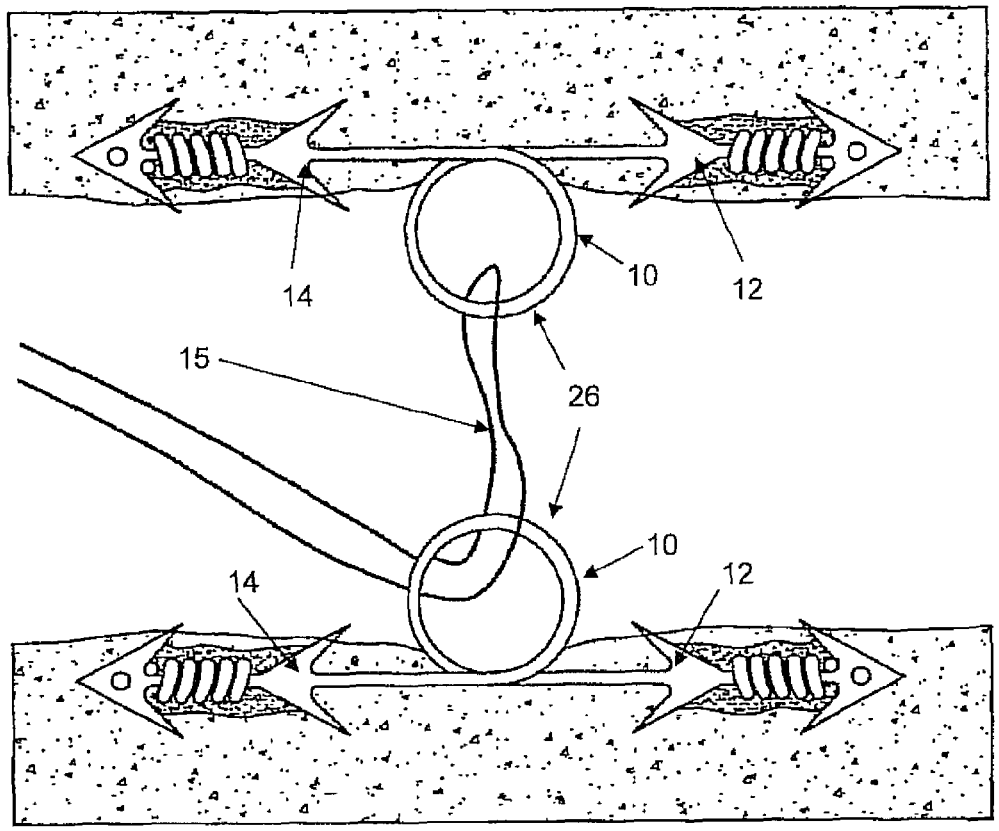
FIGS. 24 A-C are side views showing the manner in which a tissue defect is corrected using the tissue tacks of the present invention.
Figure 24B:
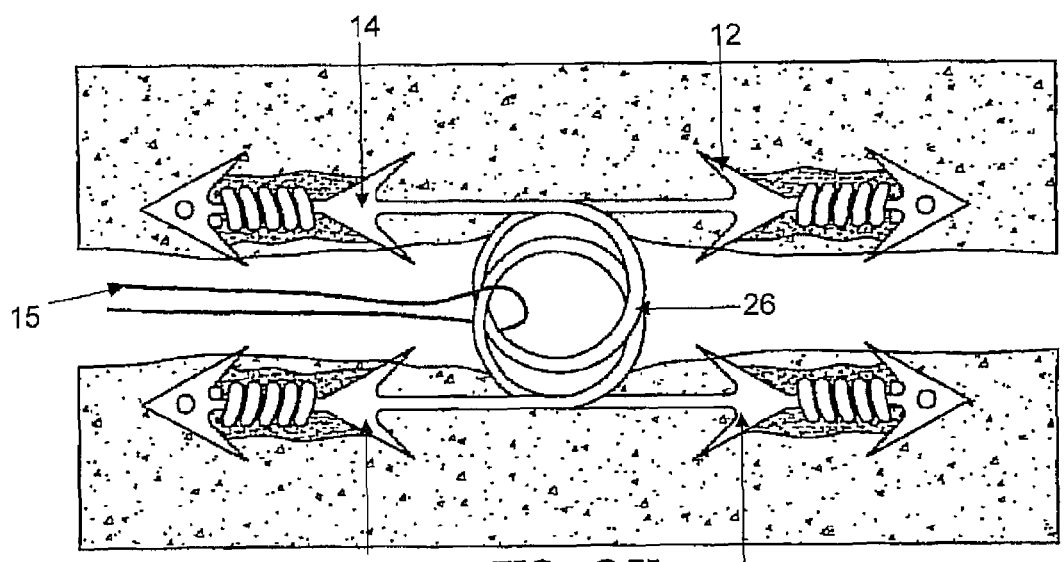

Alternatively, as shown in FIG. 24, two or more tissue tacks 10 can be placed on opposite sides of damaged tissue. Subsequent to deployment, surgical thread, sutures, staples, bands, and other similar devices, can be woven or threaded through the tissue tacks 10. The one can pull the tissue tacks 10 into close proximity, thereby fixing the damaged tissue. Once the damage has been repaired, a knot, collar, crimp, or other similar device capable of preventing the thread from coming undone is affixed on the end of the thread. Alternatively, the ends of the thread can be affixed to one another, such as for example via heating, bonding, or magnetically adhering the ends to one another.

Figure 25B:
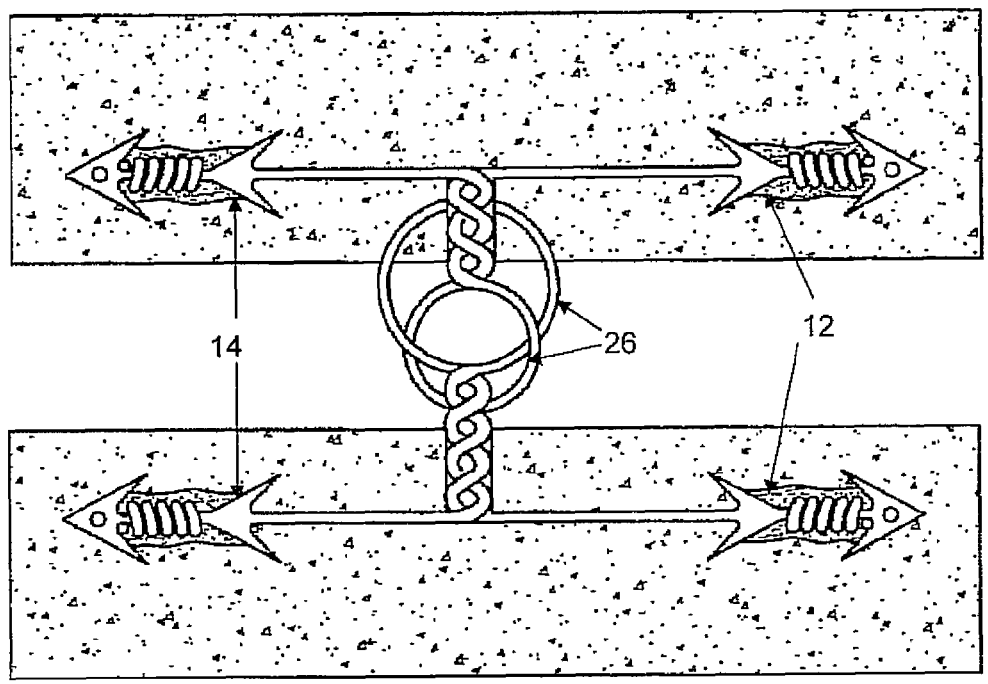
FIGS. 25 A-C are side views showing an alternative manner in which a tissue defect is corrected using the tissue tacks of the present invention.
Figure 25C:
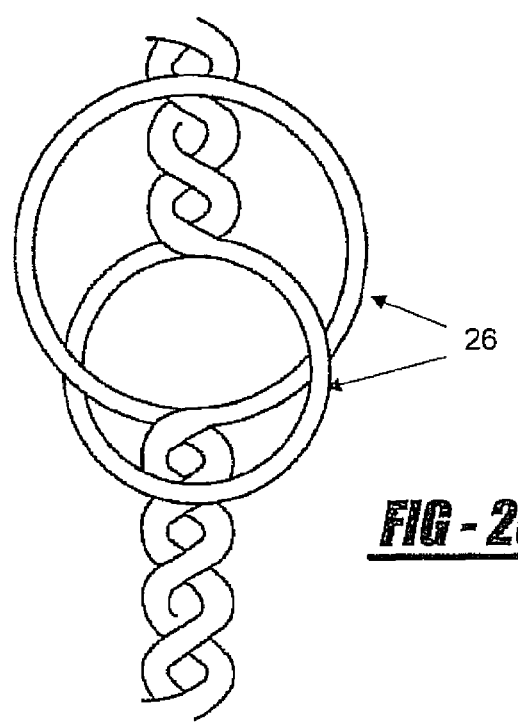
Figure 27:
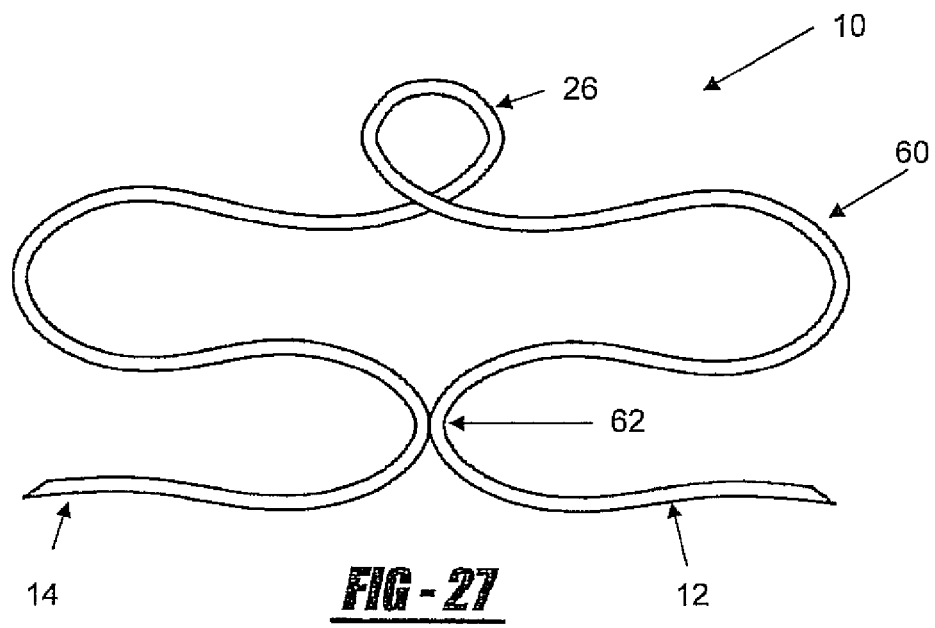
FIG. 27 is a side view showing an alternative embodiment of the tissue tack of the present invention.

Further, as shown in FIG. 25, multiple tissue tacks 10 can be interconnected. The interconnection, as shown, is achieved by inserting the anchoring mechanism 26 of a first tissue tack 10 into the anchoring mechanism 26 of a second tissue tack 10'. Since, the anchoring mechanism 26 is made of a pliable material, the interconnection is easy to achieve. Preferably, the anchoring mechanism 26 of the first tissue tack is larger than the anchoring mechanism 26 of the second tissue tack 10', thereby preventing the first tissue tack 10 from backing out of the interconnection.

The present invention is beneficial because the surgeon can perform the therapy in a beating heart and the surgeon can see how the therapy affects the patient in an objective way. The surgeon can select the kind and size of weave depending where the tissue tack going to work, the surgeon can see the weave in all the layers, and also where the sutures arrive (the present surgeon can only see the surfaces). Also, verification can occur to see if the therapy/treatment is working on the heart conduction system. The surgeon is also able to plan and modify the therapy/treatment with opportune information in real time.

A further advantage of the present invention is that the puncturing ends 18,20 can be used as a temporal or definitive pacemaker, thanks to the form of the tissue tack 10, and its manner of implantation. Since the implantation of the anchor is atraumatic, this allows an optimal bioelectric contact, where myocardial cell is not affected with an excellent contact, producing a good myocardic answer by an effective energy transmission. The battery life is thereby extended in a significant way. In other words, the patient receives a fully compatible electrophysiological system, with a better physiological answer and greater battery life.

More specifically, the currently available separator that allows the surgeon a good vision of the operating field is replaced by the three-dimensional images in real time. The surgical forceps are replaced by a vacuum system that allows the surgeon to stabilize and move the different weaves. The thread, needles, and carry needles forceps are replaced by tissue tacks 10 allowing the realization of continuous suture.

The advantage of this system is not only its size and versatility, it also allows removal of them, so they can float in the site of administration until deployment or the tissue tack 10 can be removed if necessary.

Throughout this application, author and year and patents by number reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of deploying a plurality of tissue fixation devices, the method comprising:
    loading a first tissue fixation device into a deployment gun, wherein the first tissue fixation device is formed of a single piece of material formed into a shape including:
        a loop anchor member for anchoring the device in tissue and preventing migration thereof, and
        at least two flexible arms attached directly to the loop anchor member and extending away from the loop anchor member, wherein the arms are arranged for entry into tissue during a procedure, and
        wherein the arms are arranged to be forced together in parallel within a deployment device, and to extend outwardly in opposite directions when deployed within at least one layer of tissue;
    actuating trigger means of the deployment gun;
    driving the first tissue fixation device linearly along a hollow barrel of the deployment gun and spirally into tissue with guide means,
    loading a second tissue fixation device into the deployment gun; and
    driving the second tissue fixation device along the hollow barrel of the deployment gun and spirally into the tissue, including threading the second tissue fixation device through the first tissue fixation device.

2. The method according to claim 1, further including inserting the deployment gun into a trocar disposed in an incision.

3. The method according to claim 1, further including imaging the location of the deployment gun by a method chosen from the group consisting of ultrasound, magnetic resonance imaging, CT, X-ray, fluoroscopy, and nuclear imaging.

4. The method according to claim 1, wherein the driving includes driving the tissue fixation device with arms straightened and forced together along the hollow barrel and into tissue, and opening and extending the arms in opposite directions.

5. The method according to claim 1, further including loading the tissue fixation device onto the hollow barrel of the deployment gun.

6. The method according to claim 1, wherein the actuating and driving are performed during an anastomosis procedure.

* * * * *

UNITED STATES PATENT AND TRADEMARK OFFICE
CERTIFICATE OF CORRECTION

PATENT NO.      : 8,491,631 B2
APPLICATION NO. : 12/162633
DATED           : July 23, 2013
INVENTOR(S)     : Pedro J. Del Nido et al.

Page 1 of 1

It is certified that error appears in the above-identified patent and that said Letters Patent is hereby corrected as shown below:

On the title page, item (22), column 1 (PCT Filed), line 1, delete "Jan. 3, 2007" and insert
-- Jan. 30, 2007 --

Signed and Sealed this
Twenty-second Day of October, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,491,631 B2 | Page 1 of 1 |
| APPLICATION NO. | : 12/162633 | |
| DATED | : July 23, 2013 | |
| INVENTOR(S) | : del Nido et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 719 days.

Signed and Sealed this
Seventeenth Day of February, 2015

Michelle K. Lee
*Deputy Director of the United States Patent and Trademark Office*